(12) United States Patent
Dods et al.

(10) Patent No.: US 10,341,483 B2
(45) Date of Patent: Jul. 2, 2019

(54) METHOD AND MOBILE TRANSCEIVER PROVIDING CONTAINER SECURITY

(71) Applicant: BlackBerry Limited, Waterloo (CA)

(72) Inventors: Jeffrey Alton Hugh Dods, Kitchener (CA); Robert George Oliver, Waterloo (CA); Nazih Almalki, Waterloo (CA)

(73) Assignee: BlackBerry Limited, Waterloo (CA)

( * ) Notice: Subject to any disclaimer, the term of this patent is extended or adjusted under 35 U.S.C. 154(b) by 44 days.

(21) Appl. No.: 15/230,881

(22) Filed: Aug. 8, 2016

(65) Prior Publication Data

US 2018/0041626 A1    Feb. 8, 2018

(51) Int. Cl.

| | |
|---|---|
| *H04M 1/725* | (2006.01) |
| *H04W 76/27* | (2018.01) |
| *H04W 68/00* | (2009.01) |
| *A61B 6/00* | (2006.01) |
| *G01T 7/00* | (2006.01) |
| *H04M 11/00* | (2006.01) |

(52) U.S. Cl.
CPC ....... *H04M 1/72533* (2013.01); *A61B 6/4258* (2013.01); *G01T 7/00* (2013.01); *H04M 11/00* (2013.01); *H04W 68/005* (2013.01); *H04W 76/27* (2018.02)

(58) Field of Classification Search
None
See application file for complete search history.

(56) References Cited

U.S. PATENT DOCUMENTS

| | | | | |
|---|---|---|---|---|
| 3,009,138 | A  * | 11/1961 | Lindsay | G08B 13/181 105/394 |
| 3,197,632 | A  * | 7/1965 | Baughman | B61K 9/04 116/202 |
| 6,153,884 | A  * | 11/2000 | Czimmek | G01T 1/185 250/336.1 |
| 2003/0227382 | A1 * | 12/2003 | Breed | G06Q 20/203 340/539.13 |
| 2005/0046567 | A1 | 3/2005 | Mortenson et al. | |
| 2005/0248456 | A1 * | 11/2005 | Britton, Jr. | G06Q 10/08 340/539.29 |

(Continued)

OTHER PUBLICATIONS

Notification of Transmittal of the International Search Report and Written opinion; PCT/CA2017/050932; dated Nov. 14, 2017.

(Continued)

*Primary Examiner* — Alejandro Rivero
(74) *Attorney, Agent, or Firm* — Ridout and Maybee LLP

(57) ABSTRACT

A method and mobile transceiver providing container security is described. In accordance with one aspect, there is provided a method of operating a mobile transceiver comprising a processor, memory, wireless transceiver and radiation detector. The method comprises detecting, by the radiation detector, radiation emitted from a radioactive emitter. The radiation detector and the radioactive emitter are arranged such that a substantially constant rate of radiation from the radioactive emitter is detected when one or more doors of the shipping container are closed. When the detected radiation is outside a tolerance of the constant rate, the processor wakes up the processor from a low power mode, and updates an asset tracking log stored in the memory by adding a record representing a door open event.

25 Claims, 11 Drawing Sheets

(56) References Cited

U.S. PATENT DOCUMENTS

| | | |
|---|---|---|
| 2006/0181413 A1 | 8/2006 | Mostov |
| 2008/0100706 A1 | 5/2008 | Breed |
| 2009/0015400 A1 | 1/2009 | Breed |
| 2010/0163731 A1 | 1/2010 | Haran et al. |
| 2013/0187777 A1 | 7/2013 | Bennett et al. |
| 2013/0249710 A1 | 9/2013 | Johnson et al. |

OTHER PUBLICATIONS

International Preliminary Report on Patentability; PCT/CA2017/050932 dated Feb. 21, 2019.
Extended European Search Report; EP17838253.7; dated May 17, 2019.
Simplysafe: "Will the Entry Sensors work with all types of windows and doors", WebArchive', XP055585328; :https://web.archive.org/web/20160717163717/https://simplisafe.com/help-center/result/will-entry- sensors-work-with-all-types-windows-and-doors-can-you-provide-some-exa [retrieved on May 3, 2019] Jul. 17, 2016.

* cited by examiner

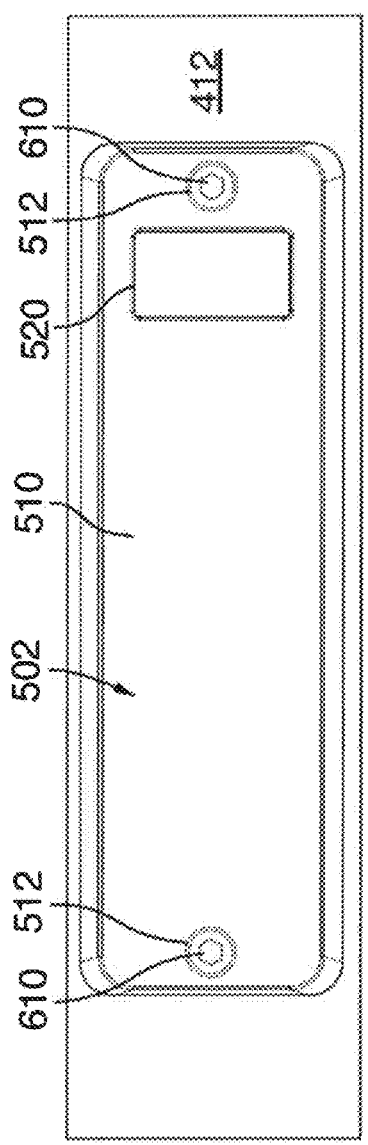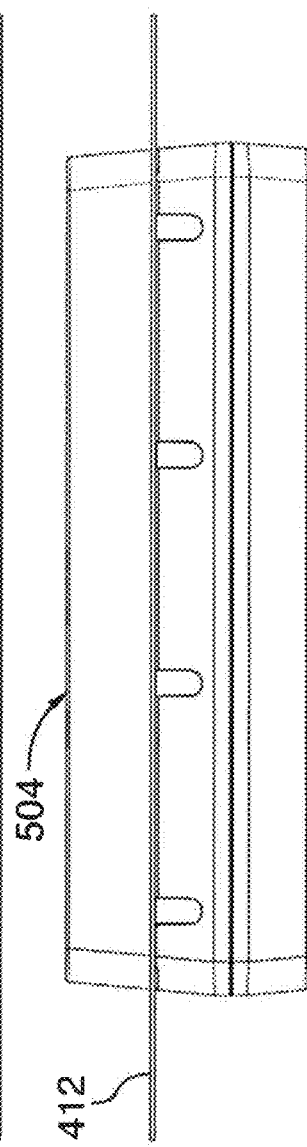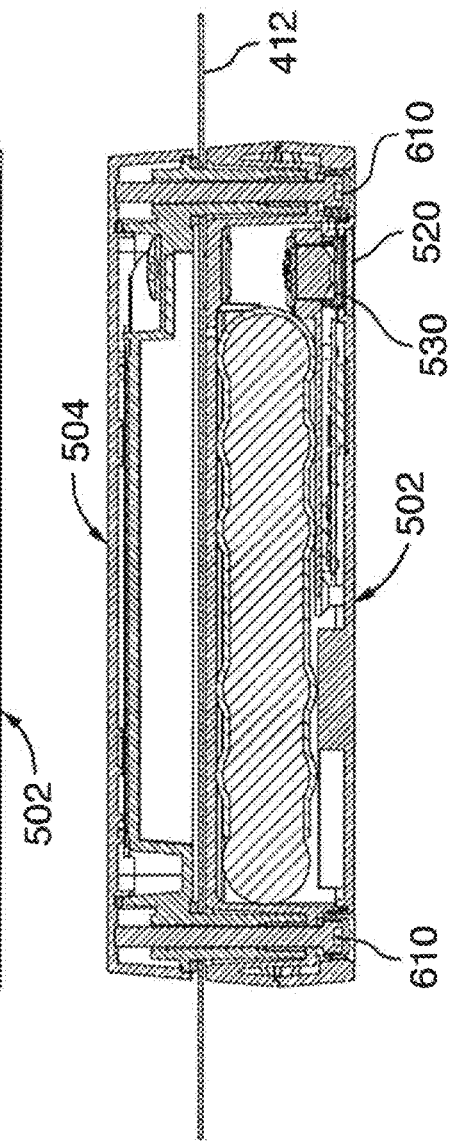

METHOD AND MOBILE TRANSCEIVER PROVIDING CONTAINER SECURITY

TECHNICAL FIELD

The present disclosure relates generally to a mobile transceiver, and more specifically, to a method and mobile transceiver providing container security.

BACKGROUND

Global Navigation Satellite System (GNSS) tracking devices, such as Global positioning system (GPS) tracking devices, are devices carried by objects or persons ("carriers") which measure the location of the carrier using the GNSS at regular intervals and typically store the location in internal memory. There are three main types of GNSS tracking devices: a data logger, a data pusher and a data puller. A data logger stores the measured location data in internal memory for subsequent download and analysis. A data pusher (also known as a beacon) sends location data stored in internal memory to a server or other device in accordance with predefined parameters. A data puller (also known as a transponder) stores location data in internal memory and provides the location data in response to queries from a server or other device.

GNSS tracking devices typically have limited power and/or limited processing resources. Accordingly, methods of efficiently operating and deploying GNSS tracking devices are desirable.

BRIEF DESCRIPTION OF THE DRAWINGS

FIG. 6A is a front view of the mobile transceiver housing of FIG. 5 mounted to a door of the shipping container of FIG. 4 viewed from the interior of the shipping container.

FIG. 6B is a side view of the mobile transceiver housing of FIG. 5 mounted to a door of the shipping container of FIG. 4.

FIG. 6C is a sectional view of the mobile transceiver housing of FIG. 5 mounted to a door of the shipping container of FIG. 4.

DESCRIPTION OF EXAMPLE EMBODIMENTS

Figure 1:
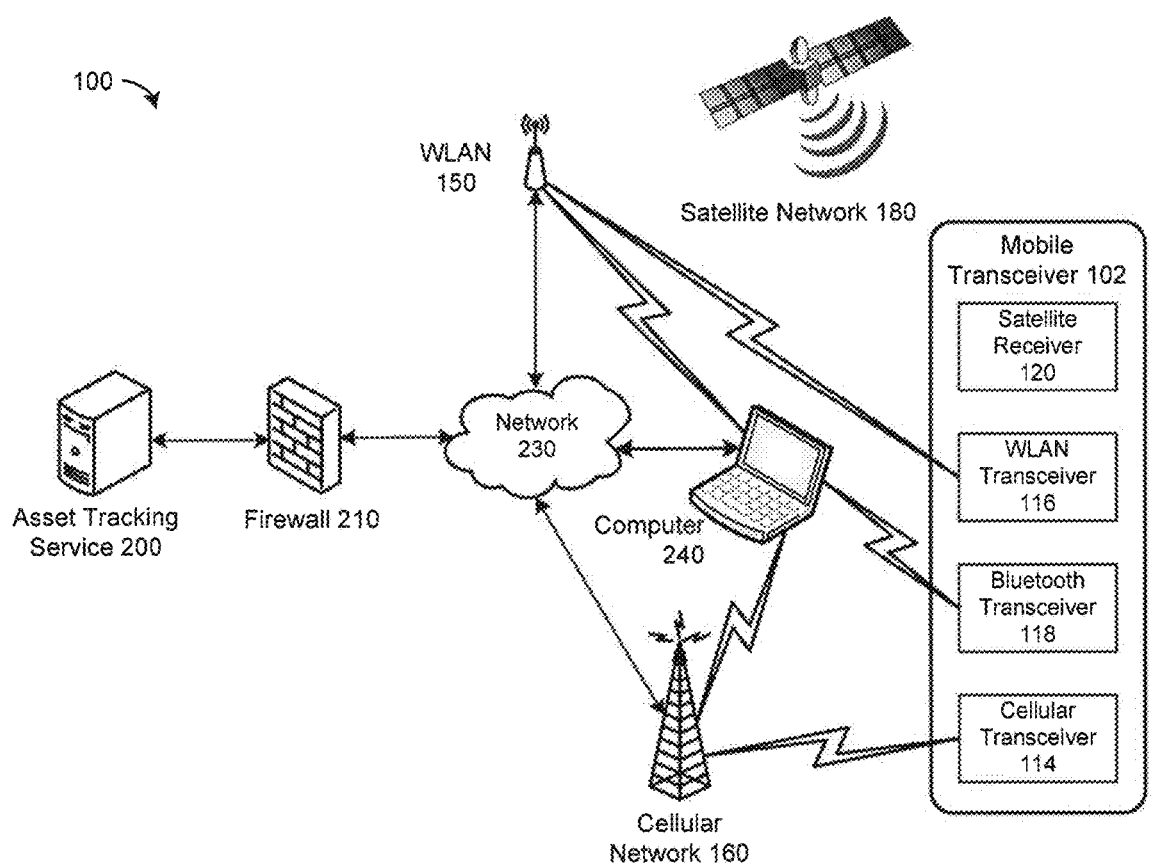
FIG. 1 is a block diagram illustrating a communication system suitable for operating a mobile transceiver in accordance with the present disclosure.

The present disclosure is made with reference to the accompanying drawings, in which embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements, operations or steps in alternative embodiments. Separate boxes or illustrated separation of functional elements of illustrated systems and devices does not necessarily require physical separation of such functions, as communication between such elements can occur by way of messaging, function calls, shared memory space, and so on, without any such physical separation. As such, functions need not be implemented in physically or logically separated platforms, although illustrated separately for ease of explanation herein. Different devices can have different designs, such that while some devices implement some functions in fixed function hardware, other devices can implement such functions in a programmable processor with code obtained from a machine readable medium.

The present disclosure provides a mobile transceiver that may allow global and long-range tracking applications in which an asset in global and long-range transit can be tracked even though it crosses wireless carrier and network coverage boundaries while in transit. In global and long-range tracking applications the mobile transceiver and the asset being tracked may cross wireless carrier and network coverage boundaries while in transit. For example, it is not uncommon for a shipping container to originate in mainland China and travel around South Africa with a final destination in North America.

The mobile transceiver of the present disclosure may be used as a tracking device to monitor shipping containers. The mobile transceiver may be mounted to the exterior of a shipping container during transit. Alternatively, the mobile transceiver may be mounted on the interior of the shipping container and an antenna may be located on the exterior of the shipping container. The mobile transceiver periodically determines its location and the location of the shipping container and possibly other data.

The shipping container may be an intermodal freight container. An intermodal freight container is a large, standardized shipping container capable of being transported using ship, rail, or truck. The container is reusable and may be used for transportation and/or storage of a variety of contents. The containers are closed boxes constructed of steel with enough strength for the boxes to be easily handled, moved, and stacked during intermodal shipping. The containers may be standardized using one of two ISO standards: ISO 668:2013 Series 1 freight containers and ISO 1496-1: 2013 Series 1 freight containers. Standard intermodal freight containers have exterior dimensions of 20 ft or 40 ft long, 8 ft wide, and 8.5 ft high. The interior of the container can be accessed using one or more of two corrugated weathering steel doors at one end which close flush to the main container's steel frame.

The containers are constructed to withstand long periods of transport or storage where the container may not be opened for months or even years at a time. Despite the strength of the steel bolts and locking hardware, theft of the container contents is a major international concern. In many scenarios, locks may be broken, or the pins removed which hold the doors to the hinges to gain unauthorized access to the contents of the container.

In accordance with a first aspect of the present disclosure, there is provided a method of operating a mobile transceiver. In accordance with one embodiment, the method comprises detecting, by the radiation detector, radiation emitted from a radioactive emitter. The radiation detector and the radioactive emitter are arranged such that a substantially constant rate of radiation from the radioactive emitter is detected when one or more doors of the shipping container are closed. The radioactive emitter and radiation detector and are mounted in, on, or about the door or doors of the shipping container so as to be aligned with each other so that a substantially constant rate of radiation from the radioactive emitter is detected when one or more doors of the shipping container are closed. In some example embodiments, one of the radioactive emitter and radiation detector is located in a door frame of the shipping container and the other of the radioactive emitter and radiation detector is located in an outer edge of the door.

When the detected radiation is within a tolerance of the constant rate, this indicates that the door is closed. When the detected radiation is outside the tolerance of the constant rate (typically below the substantially constant rate), this indicates a door open condition. When the detected radiation is outside a tolerance of the constant rate, the processor wakes up the processor from a low power mode, and updates an asset tracking log stored in the memory by adding a record representing a door open event.

Existing devices to monitor the door status of shipping containers are either easily circumvented or too costly in terms of power consumption. For example, simple magnetic or mechanical trips or switches, while power efficient, are easily circumvented. However, more sophisticated methods, such as beam-breaking optical sensors and micro electromechanical systems (MEMS) sensors like accelerometers, gyroscopes and magnetometers, require too much power to monitor the door status of a shipping container over long periods when an external power source is not available. The present disclosure provides a power efficient approach to container security which utilizes a radioactive emitter and radiation detector pair in determining the door status.

In accordance with another embodiment of the first aspect of the present disclosure, there is provided a method of operating a mobile transceiver having a processor, a wireless transceiver, an internal antenna and an external antenna each coupled to the wireless transceiver via a switch, wherein the mobile transceiver is a two-part, interconnected module, configured to be mounted to a door of a shipping container, a radiation detector, and a radioactive emitter monitoring a condition of the door of the shipping container, wherein the interconnected module comprises an internal module to be located on an interior of the door of the shipping container and which carries the internal antenna, and an external module to be located on an exterior of the door of the shipping container and which carries the external antenna, the method comprising: waking up the mobile transceiver upon detection of a change in the condition of the door; determining whether the door of the shipping container to which the mobile transceiver is mounted is in an open condition or a closed condition; switching to the external antenna as an active antenna when the door of the shipping container to which the mobile transceiver is mounted is determined to be in the closed condition; and switching to the internal antenna as the active antenna when the door of the shipping container to which the mobile transceiver is mounted is determined to be in the open condition.

In accordance with another aspect of the present disclosure, there is provided a mobile transceiver comprising a processor, a memory, a wireless transceiver, and a radiation detector, the memory having tangibly stored thereon executable instructions that, when executed by the processor of the mobile transceiver, cause the mobile transceiver to perform the methods described above and herein.

In accordance with a further aspect of the present disclosure, there is provided a non-transitory machine readable medium having tangibly stored thereon executable instructions that, when executed by a processor of a mobile transceiver, cause the mobile transceiver to perform the methods described above and herein.

In accordance with yet a further aspect of the present disclosure, there is provided a system, comprising: a radiation detector placed within a door frame having a field of view across a door opening; a radioactive emitter placed along an edge of the door such that when the door is closed, the radioactive emitter emits radiation into the radiation detector; and a processor electrically coupled to a radiation detector and receiving a closed door signal therefrom in response to the radioactive emitter emitting radiation into the radiation detector.

Figure 2:
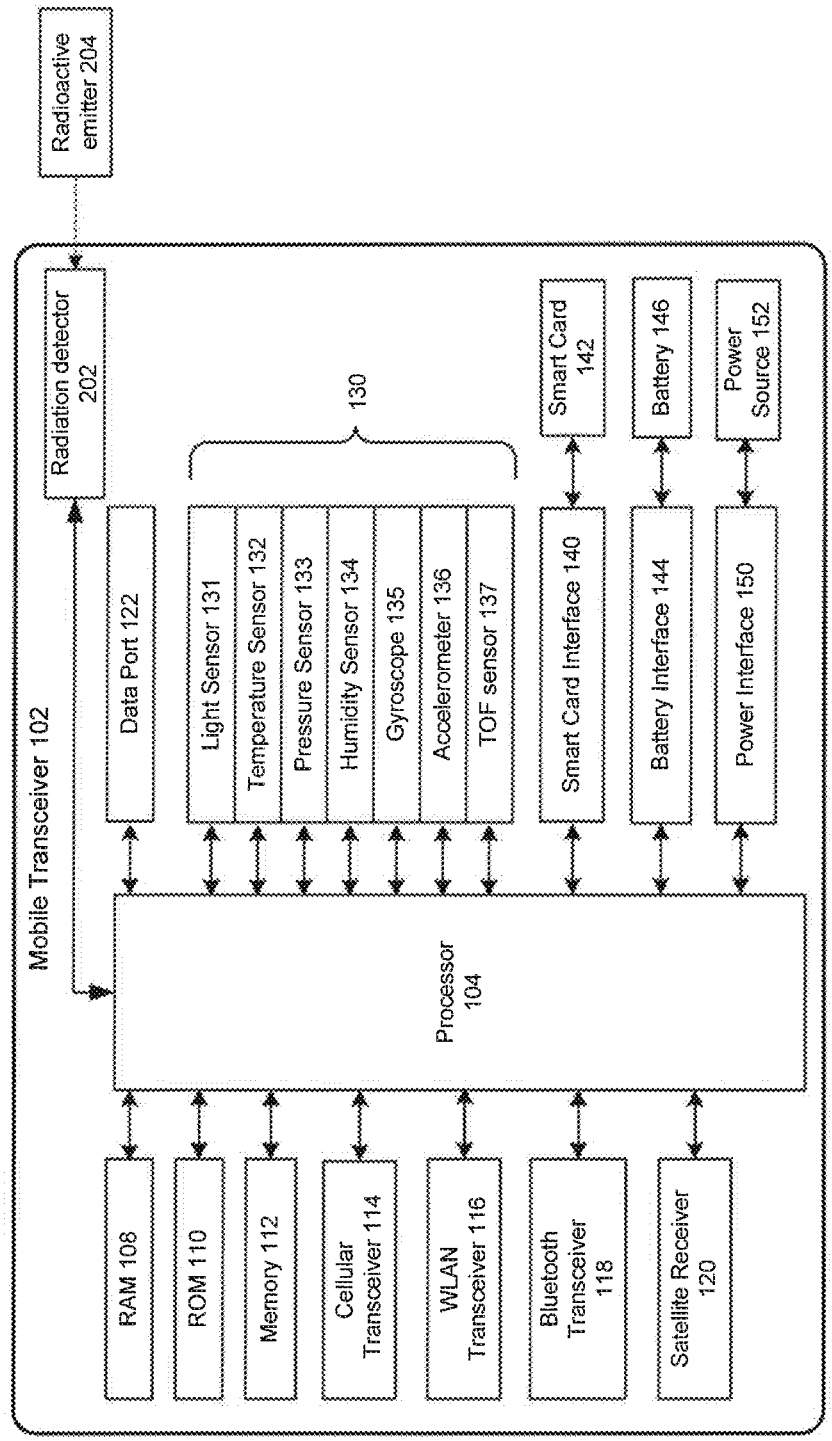
FIG. 2 is a block diagram illustrating a mobile transceiver in accordance with an example embodiment of the present disclosure.

Referring to FIGS. 1 and 2, an example embodiment of a mobile transceiver 102 of the present disclosure will be described. The mobile transceiver 102 comprises at least one processor 104 which controls the overall operation of the mobile transceiver 102. The processor 104 is coupled to a plurality of components via a communication bus (not shown) which provides a communication path between the components and the processor 104. The mobile transceiver 102 also comprises a Random Access Memory (RAM) 108, Read Only Memory (ROM) 110, a persistent (non-volatile) memory 112 which may be flash erasable programmable read only memory (EPROM) ("flash memory") or other suitable form of memory, a data port 122 such as a serial data port (e.g., Universal Serial Bus (USB) data port), and a plurality of environmental sensors 130 for sensing the environment of the mobile transceiver 102. The sensors 130 may comprise a light sensor 131, temperature sensor 132, pressure sensor 133, humidity sensor 134, gyroscope 135, accelerometer 136, one or more time-of-flight (ToF) sensors 137 and other sensors such as a radiation detector 202.

The mobile transceiver 102 also comprises a satellite receiver 120 for receiving satellite signals from a satellite network 180 that comprises a plurality of satellites forming part of a global or regional satellite navigation system. In some embodiments, a satellite transceiver capable of both receiving and sending satellite signals may be provided instead of a satellite receiver which can only receive satellite signals.

The mobile transceiver 102 can use signals received by the satellite receiver 120 from a plurality of satellites in the satellite network 180 to determine its position. In at least some embodiments, the satellite network 180 comprises a plurality of satellites which are part of at least one Global Navigation Satellite System (GNSS) that provides autonomous geo-spatial positioning with global coverage. For example, the satellite network 180 may be a constellation of GNSS satellites. Example GNSSs include the United States NAVSTAR Global Positioning System (GPS) or the Russian GLObal NAvigation Satellite System (GLONASS). Other satellite navigation systems which have been deployed or which are in development include the European Union's Galileo positioning system, China's BeiDou Navigation Satellite System (BDS), the Indian regional satellite navigation system, and the Japanese satellite navigation system.

The mobile transceiver 102 also comprises one or more wireless transceivers for exchanging at least data communication. The wireless transceivers comprises at least a cellular (RF) transceiver 114 for communicating with a plurality of different radio access networks (RAN) such as a cellular network 160 using different wireless data communication protocols and standards. The mobile transceiver 102 may communicate with any one of a plurality of fixed transceiver base stations (one of which is shown in FIG. 1) of the cellular network 160 within its geographic coverage area. The mobile transceiver 102 may send and receive signals over the cellular network 160 after the required network registration and/or activation procedures have been completed. In the described embodiment, the cellular transceiver 114 is a multi-band transceiver that supports multiple radio frequency bands which may include, for example, multiple 4G Long-Term Evolution (LTE) or LTE Advanced bands as well as global 3G and 2G bands such as, for example, a TOBY-L2 series wireless transceiver from u-blox Holding AG of Switzerland. In other embodiments, multiple dedicated transceivers may be provided to support different wireless services, such as 4G LTE, 3G and 2G wireless services.

Examples of technologies that can be used by the cellular transceiver 114 include LTE, LTE Advanced, General Packet Radio Service (GPRS), Mobitex™, and Data TAC™. The above-noted technologies are used by example and are not exhaustive. The described embodiments do not depend on any particular characteristics or capabilities of the RAN.

The wireless transceivers may also comprise a wireless local area network (WLAN) transceiver 116 for communicating with a WLAN 150 via a WLAN access point (AP). The WLAN 150 may comprise a Wi-Fi wireless network which conforms to IEEE 802.11x standards (sometimes referred to as Wi-Fi®). Other communication protocols may be used for the WLAN 104 in other embodiments.

The wireless transceivers may also comprise a short-range wireless transceiver, such as a Bluetooth® transceiver 118, for communicating with a computer 240. The mobile transceiver 102 may alternatively communicate with the computer 240 using a physical link such as the data port 122 (e.g., USB port).

Data received by the mobile transceiver 102 may be decompressed and decrypted by a decoder (not shown). The communication subsystem of the mobile transceiver 102 also includes one or more antennas, a processor such as a digital signal processor (DSP), and local oscillators (LOs). The specific design and implementation of the communication subsystem is dependent upon the wireless communication technologies implemented by the mobile transceiver 102.

Network access requirements vary depending upon the type of cellular network 160. In the described embodiment, the mobile transceiver 102 includes a smart card interface 140 for receiving a smart card 142 for storing and reading data by the processor 104.

The mobile transceiver 102 also includes a battery 146 as a power source. The battery 146 may be a rechargeable or non-rechargeable battery. The battery 146 provides electrical power to at least some of the components of the mobile transceiver 102. A battery interface 144 provides a mechanical and electrical connection for the battery 146. The battery interface 144 may be coupled to a regulator (not shown) which provides power V+ to the circuitry of the mobile transceiver 102. In some embodiments, the battery 146 is a large-capacity, non-rechargeable, sealed battery which is expected to have a relatively long service life, such as 5-7 years of active service.

The mobile transceiver 102 may also include a power interface, such as a power port, for connecting to an external power source 152 such as an alternating current (AC) power adapter. The mobile transceiver 102 can use the external power source 152 rather than the battery 146. If the battery 146 is rechargeable, the external power source 152 may be used to recharge the battery 146.

Referring again to FIG. 1, an example communication system 100 in which a mobile transceiver 102 of the present disclosure can operate will be described. The mobile transceiver 102 typically uses the cellular network 160 to access an asset tracking service (e.g., a server or fleet management system) 200. The asset tracking service 200 may be implemented as one or more server modules and is typically located behind a firewall 210. The asset tracking service 200 provides administrative control and management capabilities over a plurality of managed mobile transceivers 102. The asset tracking service 200 may be embodied as a variety of configurations, in hardware or software, including a server-based system, an Application Programming Interface (API) and/or endpoint that provides access and abstraction of the functionality of asset tracking service 200 such that no hardware or configuration information is necessary to access the functionality other than the API location and functional definitions.

The asset tracking service 200 provides secure transmission of data exchanged between the asset tracking service 200 and the plurality of managed mobile transceivers 102. Communication between the asset tracking service 200 and the mobile transceivers 102 may be encrypted, for example, using Advanced Encryption Standard (AES) or Triple Data Encryption Standard (Triple DES) encryption.

The mobile transceiver 102 uses signals received by the satellite receiver 120 from a plurality of satellites in the satellite network 180 to determine its position. For example, the mobile transceiver 102 may use the satellite receiver 120 to determine is location at regular intervals, in accordance with a predefined schedule, or in response to a trigger event, among other possibilities. The frequency or schedule at which the location is determined may be fixed or configurable. The mobile transceiver 102 stores the determined location, typically in terms of Latitude and Longitude, and a time at which the location was determined in a data log stored in the memory 112 of the mobile transceiver 102. Thus, the data log provides an asset tracking log.

The mobile transceiver 102 may also use one or more of the sensors 130 to sense or measure an environment of the mobile transceiver 102. For example, the sensors 130 may be used to measure temperature, pressure and humidity, as well as door open or movement events, among other parameters. The sensor data obtained via the sensors 130 and a time at which the sensor data was obtained are also stored in the data log (e.g., the asset tracking log), which is stored in the memory 112. As with the location data, the mobile transceiver 102 may collect sensor data at regular intervals, in accordance with a predefined schedule, or in response to a trigger event, among other possibilities. The frequency or schedule at which sensor data is obtained may be fixed or configurable and may be based in-part on the battery life remaining.

The mobile transceiver 102 attempts to connect to the asset tracking service 200 to report location and/or sensor data stored in the asset tracking log at regular intervals, in accordance with a predefined schedule, or in response to a trigger event, such as a door ajar detection signal, among other possibilities. The frequency or schedule at which the mobile transceiver 102 attempts to connect to the asset tracking service 200 may be fixed or configurable and may be based in-part on the battery life remaining. The mobile transceiver 102 typically attempts to connect to the asset tracking service 200 using a wireless transceiver such as the cellular transceiver 114. The mobile transceiver 102 has access to multiple wireless services provided by multiple wireless transceivers, each of which provides access to one or more wireless services. In the described embodiment, the multiple wireless transceivers comprise the cellular transceiver 114, WLAN transceiver 116, and Bluetooth transceiver 118. The wireless transceivers may include multiple cellular transceivers 114 in some embodiments, which may be multi-band cellular transceivers 114. The mobile transceiver 102 could also attempt to connect to the asset tracking service 200 using a physical link, either directly or indirectly via the computer 240. Each wireless service supported by the mobile transceiver 102 may be defined by a standard or specification. Non-limiting examples of wireless service described elsewhere in the present disclosure and include 4G Long-Term Evolution (LTE), 3G and 2G, WLAN and Bluetooth.

When the mobile transceiver 102 connects to the cellular network 160, WLAN 150, or computer 240 via Bluetooth and/or USB, the mobile transceiver 102 can send the data log or a portion of the data log (e.g., an unreported portion of the data log) to the asset tracking service 200 through the firewall 210 using a communication network 230. The data log information may be sent using any suitable message format including, for example, a proprietary message format. The mobile transceiver 102 data log typically includes an indicator regarding which data in the data log has been reported and which data in the data log is unreported. For example, in some embodiments, the data log comprises a series of records including and identified by a record identifier (ID). Each record also includes a time at which the record was made, location data and/or sensor data, and a report status indicating whether the record has been reported to the asset tracking service 200. After an unreported record is reported to the asset tracking service 200, its corresponding report status field in the data log is updated.

The mobile transceiver 102 powers-down certain device components when not in use to conserve battery power. For example, the mobile transceiver 102 initiates a low power mode for the cellular transceiver 114 after a reporting time/cycle. The low power mode may be an off mode (also known as an off state) in which the cellular transceiver 114 is unpowered or a sleep mode (also known as a standby mode or suspended operation mode) with low power consumption. The cellular transceiver 114 is then activated from the low power mode at the next reporting time/cycle. Any other wireless transceivers are similarly placed into a low power mode after a reporting time/cycle. The satellite receiver 120 and sensors 130 may also be placed into a low power mode when not obtaining location or sensor data, and then activated from the low power mode at the next measurement time/cycle.

The data logging and data reporting cycles are typically different and need not coincide, although the cycles typically overlap to varying degrees. For example, each reporting cycle typically involves reporting several records of the data log each including location data and/or sensor data. The cycles may overlap in that location data and/or sensor data may be captured as part of a common process at some times or may be captured as part of a separate process performed just prior to reporting logged data to the asset tracking service 200. For example, a wireless transceiver may be awaken for reporting at the same time, or just after, the satellite receiver 120 and/or sensors 130 are awaken and location data and/or sensor data is captured.

The communication system 100 is provided for the purpose of illustration only. The communication system 100 is but one possible configuration of a multitude of possible communication network configurations for use with the mobile transceiver 102. Suitable variations will be understood to a person of skill in the art and are intended to fall within the scope of the present disclosure. For example, while individual networks have been represented for convenience, it will be appreciated that multiple networks of each type and intermediate networks connected to the shown networks may be provided. Also, the communication links represented in FIG. 1 can be implemented using public and/or private networks that can communicate using packet data technologies, such as X.25 or Internet Protocol (IP) based addressing and routing techniques. Some connections can be implemented as secure connections, for example, using Virtual Private Network (VPN) technologies.

Figure 3A:
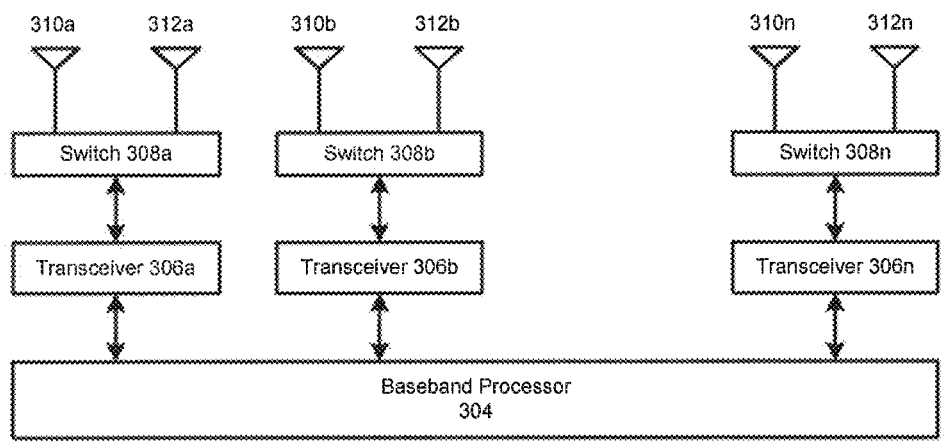
FIG. 3A is a block diagram illustrating a wireless communication subsystem in accordance with an example embodiment of the present disclosure.
Figure 3B:
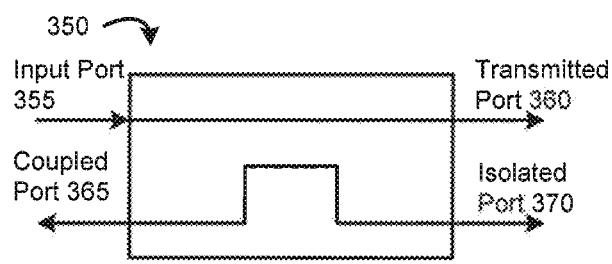
FIG. 3B is a schematic diagram of radio frequency (RF) coupler.

Referring now to FIG. 3A, a wireless communication subsystem 300 in accordance with an example embodiment of the present disclosure will be described. The wireless communication subsystem 300 includes a digital baseband processor 304 which manages functions that require an antenna, and a plurality of wireless transceivers and/or receivers 306, represented individually by references 306*a*, 306*b*, . . . 306*n*. Each of the wireless transceivers/receivers 306 is coupled to a switch 308, represented individually by references 308*a*, 308*b*, . . . 308*n*, which is coupled to an internal antenna 310, represented individually by references 310*a*, 310*b*, . . . 310*n*, and an external antenna 312, represented individually by references 312*a*, 312*b*, . . . 312*n*. The external antennas 312 typically serve as the primary antennas because of the reduced RF interference associated with being located outside of a shipping container, whereas the internal antennas 310 typically serve as secondary antennas because of the increased RF interference associated with being located inside of a shipping container. In at least some embodiments, the external antennas 312 are provided in a common external antenna module.

While a common baseband processor 304 for the cellular transceiver 114 and satellite receiver 120 has been described, in other embodiments a separate baseband processor could be provided for the satellite receiver 120 and the cellular transceiver 114. In the wireless communication subsystem 300, the cellular transceiver 114 and satellite receiver 120 are individually switched and capable of operating independently. Consequently, the satellite receiver 120 can use an external antenna 312 while the cellular transceiver 114 uses an internal antenna 310, or vice versa, the satellite receiver 120 and the cellular transceiver 114 can both use an external antennas 312, or the satellite receiver 120 and the cellular transceiver 114 can both use an internal antennas 30. The baseband processor 304, or main processor 104, selects either the internal antenna 310 or external antenna 312 for the satellite receiver 120 and the cellular transceiver 114 depending on factors such as signal quality and ancillary information from the sensors 130. Each of the wireless transceivers/receivers 306 (e.g., the satellite receiver 120 and the cellular transceiver 114) may also be separately powered-on, powered-off or placed into a sleep mode.

The terms "switch" and "switching" used in the described embodiments are not intended to be restricted to changing the active antenna. Instead, the terms are intended to include instructing a respective switch 308 to make a particular antenna the active antenna if the particular antenna is not already the active antenna. Switch 308 may comprise an electronic switch, solid state switch, or electro-mechanical (e.g., relay) depending on implementation. Switch 308 may be instructed to select various antennae by processor 104 or other circuitry, such as a communication subsystem.

While not shown, each of the wireless transceivers/receivers 306 has an RF front end circuit (also known as a transceiver module/receiver module) which generally includes all components between the antennas and the digital baseband processor 304. For example, the RF front end circuit of a cellular transceiver includes a receiver, a transmitter, and local oscillators (LOs). The receiver performs common receiver functions as signal amplification, frequency down conversion, filtering, channel selection, etc., as well as analog-to-digital conversion (ADC). The ADC of a received signal allows more complex communication functions such as demodulation and decoding to be performed by the digital baseband processor 304. In a similar manner, signals to be transmitted are processed, including modulation and encoding, for example, by the digital baseband processor 304. The processed signals are input to the transmitter for digital-to-analog conversion (DAC), frequency up conversion, filtering, amplification, and transmission via the antennas. A receiver, lacking transmitting functions, typically omits components required for receiving.

Figure 3C:
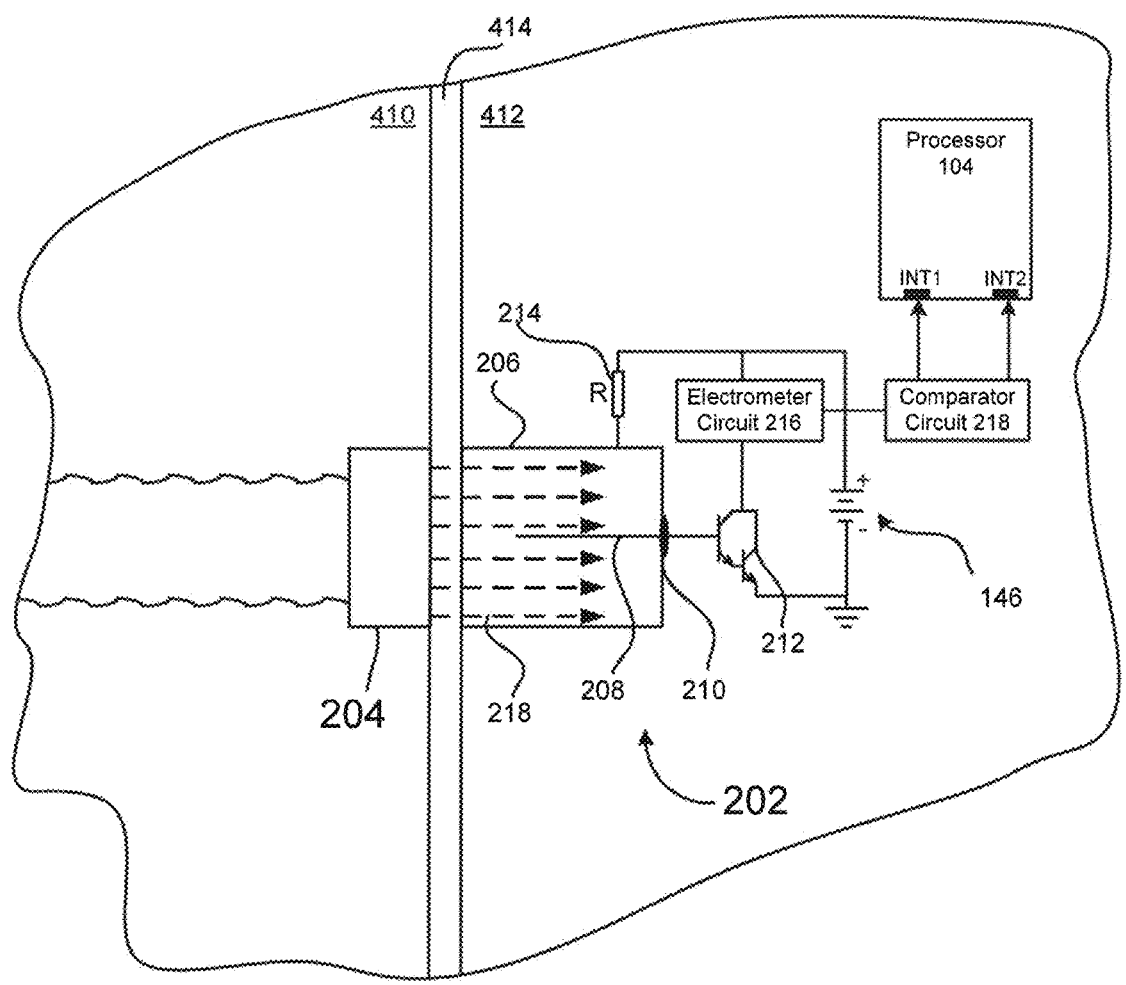
FIG. 3C is a block diagram illustrating an example circuit for a door open detector in accordance with the present disclosure.

Each cellular transceiver 114 includes an RF directional coupler in at least some embodiments. The RF directional coupler is a RF passive device used to couple a specific proportion of the power travelling in one transmission line out through another connection or port. As shown in FIG. 3C, the RF directional coupler 350 is a four port device: an input port 355, a transmitted port 360, a coupled port 365, and an isolated port 370. The RF directional coupler typically uses capacitive coupling. However, any suitable construction may be used for the RF directional coupler. The RF directional coupler 1000 may be used to sample transmission signals from an antenna (e.g., an internal antenna 310 or external antenna 312, typically using the coupled port 365, to determine whether the antenna is transmitting during a transmission. If the antenna is not transmitting during a transmission, this is an indication that the antenna has an abnormal antenna condition, for example, that the antenna may be disconnected, damaged, or has malfunctioned. If the antenna is transmitting during a transmission, this is an indication of a normal antenna condition, i.e. that the antenna is operational and functioning normally and is not damaged.

Figure 4:
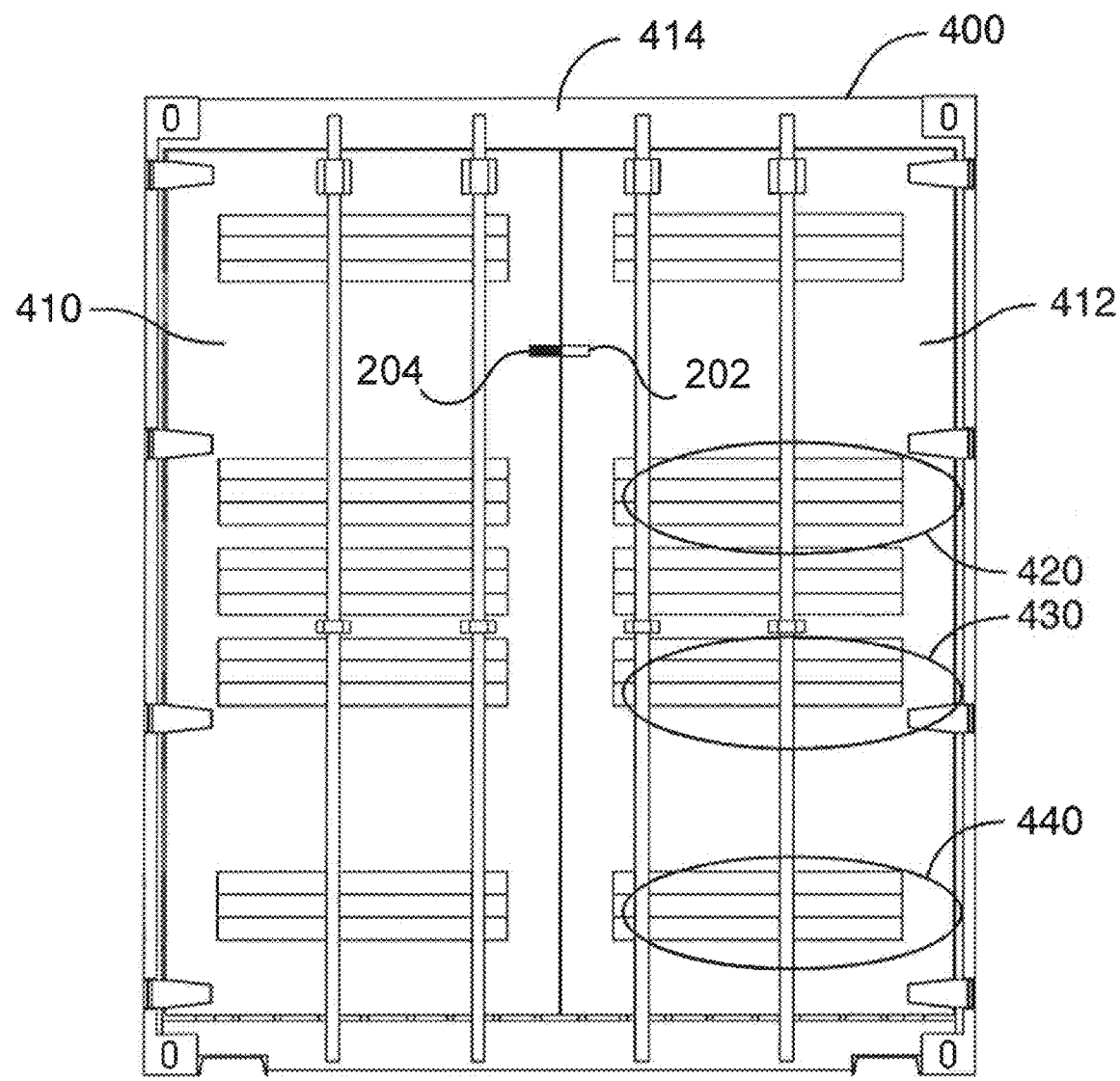
FIG. 4 is an example shipping container suitable for mounting a mobile transceiver in accordance with the present disclosure.

FIG. 4 illustrates an example shipping container 400, such as an intermodal freight container, suitable for mounting the mobile transceiver 102. The shipping container 400 includes a pair of interlocking doors 410, 412. The mobile transceiver 102 is mounted through one of the doors 410, 412 with the internal module 502 on the inside of the door 410 or 412, and the external module 504 on the outside of the door 410 or 412. Suitable mounting locations for the mobile transceiver 102 on the door 412 are represented by references 420, 430 and 440. While example mounting locations for the mobile transceiver 102 are located on the door 412, it will be appreciated that the mobile transceiver 102 could be mounted on any door of the shipping container 400, or possibly a wall of the shipping container 400. Mounting screws 610 are received in the mounting holes 512 in the front panel 510 of internal module 502 of the mobile transceiver housing 500, and are secured in thread holes (not shown) on the inside of the external module 504 of the mobile transceiver housing 500. In some embodiments, the internal module 502 and external module 504 may be further secured to the container door 412 using a suitable mounting adhesive, such as a suitable double-sided adhesive strip or tape.

Figure 5:
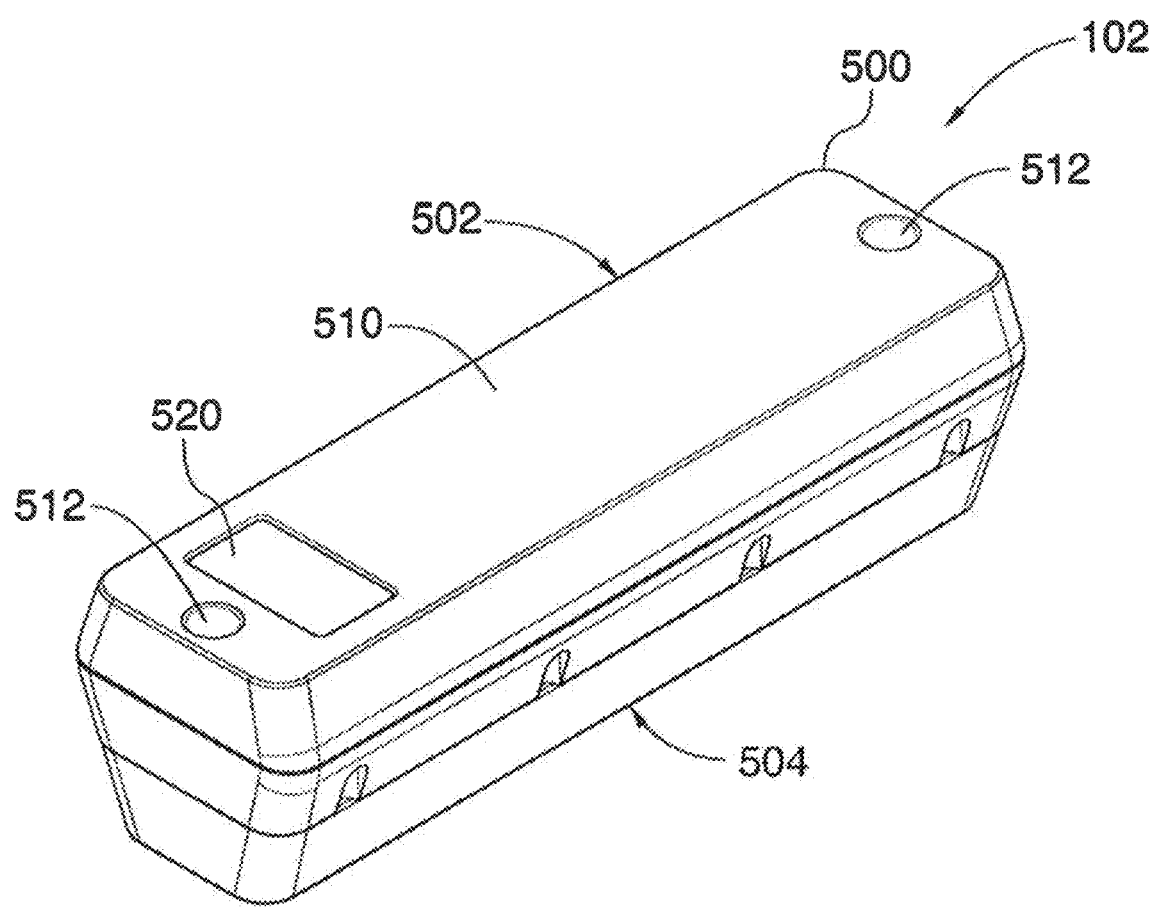
FIG. 5 is a perspective view of a mobile transceiver housing in accordance with one embodiment of the present disclosure.

FIG. 5 illustrates a mobile transceiver housing 500 of the mobile transceiver 102 in accordance with one example embodiment of the present disclosure. The housing 500 is a two-part, interconnected module, configured to be mounted to a shipping container, for example, through a door of the shipping container. The housing 500 comprises an internal module 502 and an external module 504. The internal module 502 is configured to be mounted on the interior of the shipping container, for example, on an inside surface of a door of the shipping container. The external module 504 is configured to be mounted on the exterior of the shipping container, for example, on an outside surface of the door of the shipping container. The external module carries the external antennas 312. The internal module carries the internal antennas 310, and most of the other electronic components of the mobile transceiver 102.

The internal module 502 and external module 504 are connected to each other, for example, by mounting screws (or bolts) when mounted to a shipping container 400 or other asset. A pair of mounting screws is used in the shown embodiment. A different number of mounting screws could be provided in other embodiments. In preparation for mounting the mobile transceiver 102, three holes are formed in the door of the shipping container using drilling or the like. Alternatively, the holes may be performed in the shipping container walls, ceiling, or floor. Two of the holes are provided to receive the mounting screws while the third hole is used to pass through electronics from the internal module 502, such as external antennas for the cellular transceiver 114 and satellite receiver 120 and associated circuitry, to be carried in the external module 504 in the mounted mobile transceiver 102. In the shown embodiment, two holes 512 are formed in the front panel 510 of the internal module 502 for receiving the mounting screws. Corresponding holes are located in the bottom of the internal module 502. A hole in the bottom of the internal module 502 is also provided for receiving the electronics. The front panel 510 of the internal module 502 also includes a light transmissive panel 520, such as a transparent panel.

The housing 500 defines a sensor compartment for receiving at least some of the sensors 130 located opposite to the transmissive panel 520. The sensor compartment carries the light sensor 131 and the ToF sensor 137. The sensor compartment may additionally carry the radiation detector 202. Alternatively, the radiation detector 202 may be located in a different location than the sensor compartment. For example, the radiation detector 202 may be separate from the housing 500 to allow for placement of the radiation detector 202 at a suitable location as further described below with reference to FIG. 3C.

The light sensor 131 is configured and positioned within the sensor compartment for sensing light outside of the mobile transceiver 102 through the transmissive panel 520. The ToF sensor 137 is configured and positioned within the sensor compartment for detecting objects in a first direction through the transmissive panel 520 outside of the mobile transceiver 102, e.g. within the interior of the shipping container when the mobile transceiver 102 is mounted to the shipping container. For example, the ToF sensor 137 may be used for detecting objects within the interior of the shipping container by measuring the distance between the mobile transceiver 102 and the nearest object in the first direction, and determining whether the shipper container is loaded (e.g., one or more objects detected) or unloaded (e.g., no objects detected).

FIG. 6A to 6C illustrate the mobile transceiver 102 mounted to the door 412 of the shipping container 400. FIG. 6A is a front view of the mobile transceiver housing 500 mounted to the door 412 of the shipping container 400. FIG. 6B is a side view of the mobile transceiver housing 500 mounted to the door 412 of the shipping container 400. FIG. 6C is a sectional view of the mobile transceiver housing 500 mounted to a door of the shipping container 400. The sensor compartment for receiving the light sensor 131 and ToF sensor 137 is represented by reference 530, and is located opposite to the transmissive panel 520.

Referring to FIG. 3C, the radiation detector 202 will be described in more detail. The radiation detector 202 detects ionizing radiation from a radioactive emitter 204. The radioactive emitter 204 may be a fastener in a door of the shipping container 400, such as a bolt or screw, etc. fastened within the edge of a door 410 of the shipping container 400. The radioactive fastener is typically screwed flush with the edge of the shipping container door 410 to prevent interference with the opening and closing of the door 410.

In the shown embodiment, the shipping container 400 comprises two doors 410, 412 located at one end thereof. The two doors are arranged side-by-side. The radioactive fastener is a bolt (or screw) located in an inner side edge, a door mating edge, of the door 410. The radioactive detector 202 is located in an inner side edge, a door mating edge, of the other door 412. The radioactive emitter 204 and radioactive detector 202 are aligned with each other and proximate to each other when the doors 410, 412 of the shipping container 400 are both in a closed position. The doors in which radioactive emitter 204 and radioactive detector 202 are located could be switched in other embodiments. The shipping container 400 may further comprise two doors 410, 412 located at an opposite end thereof, in which case a radioactive emitter 204 and radioactive detector 202 may be used to secure those doors as well.

In other embodiments, the radioactive fastener may be located on an outer side edge of the door 410 proximate to a door frame 414 of the shipping container 400 when closed. The radioactive emitter 204 and radiation detector 202 are aligned with each other when the door 40 is closed and within the frame 414. In yet other embodiments, the radioactive fastener may be located on a bottom or top edge of the door 410. In these alternative embodiments, the radioactive detector 202 is located proximate to the radioactive emitter 204 when the door 410 is in a closed position, and a second radioactive emitter 204 and detector 202 pair for the second door 412 of the shipping container should be provided to more fully protect it.

The radioactive fastener may be prepared by alloying a weak radioactive material with steel and plating a conventional fastener (e.g., bolt or screw) with the radioactive alloy. Alternatively, the radioactive fastener could be made entirely from the radioactive alloy. The radioactive emitter requires no external power to operate and many safe common sources have useful lifetimes of hundreds of years.

In other embodiments, rather than being a fastener in the door 410 the radioactive emitter 204 may be an element attached to or received in a hole in the door 410 and secured by a friction fit, adhesive, magnet or other fastener.

The radioactive alloy in some embodiments comprises an alloy of Americium-241 (Am), such as a steel-Am alloy. Americium-241 is a radioactive transuranic metal. Americium-241 radioactive metal is particularly suited as it emits alpha-particle radiation which is relatively safe to biological life and has a relatively short half-life of 432 years. In addition, alpha-particles emitted by Americium-241 can be detected with very low power, cheap, and small detectors. The radioactive fasteners may be made of varying isotope concentration and emission profile to decrease the chance of successfully tampering with the security mechanism, for example, the radioactive fasteners may be made of varying isotope concentrations and emission profiles so that each radioactive emitter 204 is unique.

In some embodiments, the radioactive emitter 204 comprises a steel-Am alloy with trace amounts of one or more other radioactive elements such as Iodine-131 or Strontium-90. These additional radioactive elements may create both alpha and beta sources of radiation, further increasing the number of unique radiation types and further decreasing the chance of successfully tampering with the security mechanism.

The radioactive detector 202 in at least some embodiments is an ionizing radiation detector. In some embodiments, the radioactive detector 202 is an ionization chamber. The ionization chamber comprises a gas-filled chamber with two electrodes: a cathode and an anode. In the shown embodiment, the ionization chamber is a free-air chamber that is open to atmosphere and filled with ambient air. The ionization chamber comprises a cylindrical cathode 206 and a coaxially located internal anode wire 208.

The ionization chamber is located so as to be directly opposite and aligned with the radiation emitter 204 when the doors 410, 412 are closed. For example, the ionization chamber may be located in the other door 412 of the shipping container 400 at a position corresponding to the radioactive emitter 204 when the doors 410, 412 are both closed. Alternatively, the ionization chamber may be located in the door frame 414 of the shipping container 400. The anode wire 208 is insulated from the cylindrical cathode 206 using an insulating disc 210. The battery 146 applies a voltage potential to the electrodes to create an electric field in the air within the chamber. Alternatively, a dedicated battery may be provided. A resistor 214 is present in case of a short circuit between the cylindrical cathode 206 and the anode wire 208.

The radioactive emitter 204 passes ionizing radiation 218 through the air within the ionization chamber of the radioactive detector 202. The ionizing radiation 218 produces positive ions and free electrons that move to the electrodes of the opposite polarity under the influence of the electric field, resulting in a current which is received by a transistor 212 which amplifies the current. The amplified current is then measured by an electrometer circuit 216 coupled to the processor 104.

The radioactive emitter 204 has a substantially constant rate of radiation flux. As described above, the radioactive emitter and radiation detector are mounted in, on, or about the door or doors of the shipping container so as to be aligned with each other so that a substantially constant rate of radiation from the radioactive emitter is detected when one or more doors of the shipping container are closed. Therefore, when the doors 410, 412 are closed, the radioactive detector 202 detects the substantially constant rate of radiation flux as a substantially constant current measured by the electrometer circuit 216. The substantially constant rate of radiation flux provides a basis for determining whether a door is open or closed by a comparator circuit 218. When the detected radiation is within a tolerance of the constant rate, this indicates that the door is closed. When the detected radiation is outside the tolerance of the constant rate (typically below the substantially constant rate), this indicates a door open condition. When the radioactive emitter 204 has a unique isotope concentration and emission profile, the comparator circuit 218 may be calibrated to the unique rate of radiation flux emitted by the radioactive emitter 204. Calibration data may be stored in a memory (not shown) of the comparator circuit 218.

In the shown embodiment, the comparator circuit 218 uses operational settings stored in its memory, including the constant rate and tolerance range, to generate a first interrupt signal on a first interrupt port (or pin) when the detected radiation changes from being within a tolerance of the constant rate (e.g., decrease from the constant rate) to being outside of the tolerance of the constant rate. The comparator circuit 218 also generates a second interrupt signal on a second interrupt port when the detected radiation changes from being outside of the tolerance of the constant rate to being within a tolerance of the constant rate (e.g., returns to the constant rate). The first interrupt signal indicates a misalignment between the radioactive emitter and radiation detector and the second interrupt signal indicates an alignment between the radioactive emitter and radiation detector. The first interrupt signal also indicates a door open condition and the second interrupt signal also indicates a door closed condition. In other embodiments, a single interrupt port may be used. The operational settings used by the comparator circuit 218 may be provided by the processor 104.

While in the described embodiment the radioactive detector 202 is aligned with the radioactive emitter 204 when the doors 410, 412 are closed, in other embodiments the radioactive emitter 204 and the detector 202 become aligned when the doors 410, 412 are opened. In such embodiments, the first interrupt signal would be activated when the detected radiation is within the tolerance of the constant rate than outside it, and the second interrupt signal would be activated when the detected radiation is outside the tolerance of the constant rate.

While the embodiments described above include a radioactive emitter 204 and detector 202 pair, it is contemplated that in other embodiments multiple radioactive emitters 204 may be detected by a single detector 202 or that multiple detectors 202 may be used to detected one radioactive emitter 204.

In other embodiments, one or more of the mounting screws 610 of the transceiver housing 500 may be radioactive emitters 204 with one or more radioactive detectors 202 aligned with the radioactive mounting screws 610, for example, in the front panel 510 of the internal module 502. These additional radioactive emitters 204 and detectors 202 may be used to detect that the housing 500 has been damaged or tampered with, thereby providing additional security.

Figure 7A:
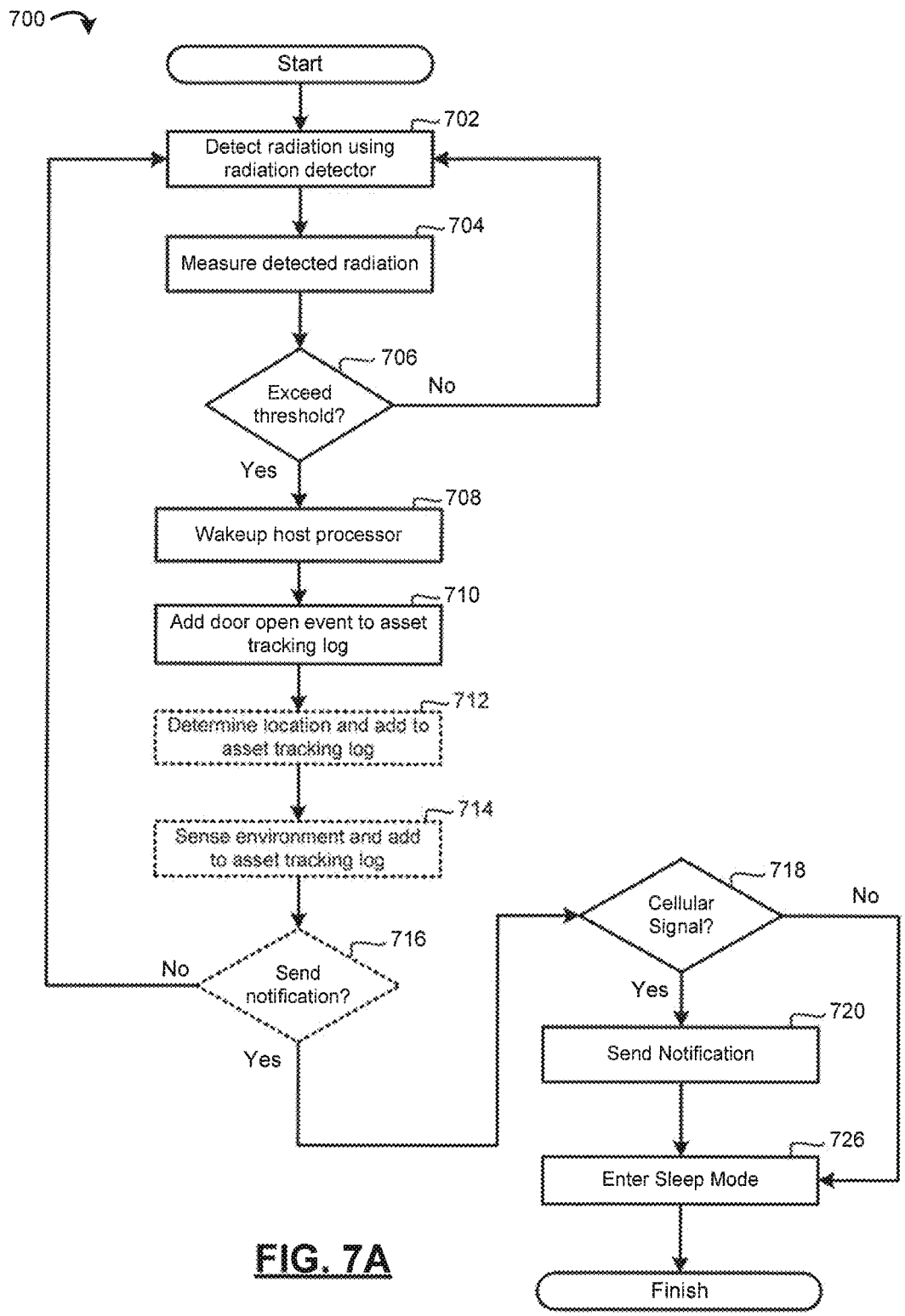
FIG. 7A to 7D are flowcharts illustrating example embodiments of a method of operating a mobile transceiver in accordance with example embodiments of the present disclosure.

FIG. 7A shows an example flowchart of a method 700 of operating a mobile transceiver 102 such as a GNSS tracking device in accordance with one example embodiment of the present disclosure. The method may be carried out by software executed by a processor of the mobile transceiver 102. Coding of software for carrying out such a method 700 is within the scope of a person of ordinary skill in the art provided the present disclosure. The method 700 may contain additional or fewer processes than shown and/or described, and may be performed in a different order in other embodiments. Machine readable code executable by the processor to perform the method 700 may be stored in a tangible machine readable medium such as a memory of the mobile transceiver 102.

At 702, the radiation detector 202 of the mobile transceiver 102 detects radiation emitted from a radioactive emitter 204, such as a radioactive screw or bolt comprised at least partially from a radioactive alloy. The radioactive alloy may be an alloy of steel and Americium-241, possibly with trace amounts of one or more of Iodine-131 or Strontium-90. The radiation detector 202 and the radioactive emitter 204 are arranged so that a substantially constant rate of radiation from the radioactive emitter 204 is detected when the doors 410, 412 of the shipping container 400 is closed. The detected radiation is within the tolerance of the constant rate when the one or more doors are closed. The detected radiation is outside of the tolerance of the constant rate, typically below the substantially constant rate of radiation, when at least one of the one or more doors is at least partially open.

At 704, the electrometer circuit 216 measures the detected radiation.

At 706, the comparator circuit 218 determines whether the measured radiation is within the tolerance of the constant rate. When the measured radiation is within the tolerance of the constant rate, this indicates the door is closed. When the measured radiation is outside of the tolerance of the constant rate, this indicates the door is at least partially open.

At 708, when the measured radiation is outside of the tolerance of the constant rate, the processor 104 wakes up (or is activated) from a low power mode (e.g., sleep mode). This typically occurs in response to the comparator circuit 218 sending the first interrupt signal to the processor 104.

At 710, the processor 104 updates the asset tracking log stored in the memory 112 by adding a record representing a door open event. The door open event includes at least a time associated with the door open event. The time is typically the time at which the first interrupt signal is received by the processor 104, which may be determined by a timestamp associated with the first interrupt signal. The timestamp may be generated by the processor 104.

The asset tracking log may take one of different forms. The asset tracking log includes a number of records. In one embodiment, each record includes a record identifier (ID), a type or reason for the record, a date and time associated with the record, and optionally location and sensor data. The type or reason specifies whether the record was generated in response to a pre-programmed wakeup event or sensor data. Pre-programmed wakeup events may be based on time (e.g., every hour) or date (e.g., once a day). The sensor data which may trigger a record include high temperature, low temperature, high humidity, low humidity, insufficient movement, too much movement, door open and door close events.

| Record ID | Type | Date and Time | Location | Sensor Data |
|---|---|---|---|---|
| 1 | Door Opened | Apr. 24 3:23 PM | 43.158° N 80.766° W | Temperature 82° F.; Humidity 15% |
| 11 | Door Closed | Apr. 24 3:37 PM | 43.158° N 80.766° W | Temperature 82° F.; Humidity 15% |
| 54 | Door Opened | May 12 10:23 PM | 43.159° N 80.764° W | Temperature 84° F.; Humidity 18% |
| 88 | Door Closed | May 12 11:53 PM | 43.159° N 80.764° W | Temperature 84° F.; Humidity 18% |

At 712, the mobile transceiver 102 optionally wakes up the satellite receiver 120 from a low power mode (e.g., sleep mode), which may be performed by the main processor 104 or the baseband processor 304, depending on the embodiment. Next, the mobile transceiver 102 determines its location using the satellite receiver, and stores the determined location and a time associated with the determined location in the asset tracking log. The determined location may be stored in the same or different record as the door open record mentioned above.

At 714, the mobile transceiver 102 optionally wakes up the sensors 130 from a low power mode (e.g., sleep mode). Next, the mobile transceiver 102 senses its environment using the one or more sensors 13, and stores the measured sensor data and a time at which the sensor data was obtained in the asset tracking log. The sensor data may be stored in the same or different record as the door open record mentioned above.

At 716, the mobile transceiver 102 optionally determines whether to send a notification message to the asset tracking service 200. This determination may be based on a number of factors including the determined location, sensor data, the next scheduled time to report to the asset tracking service 200, or a combination thereof. For example, the mobile transceiver 102 may determine whether a cellular signal is likely to be available based on the determined location.

At 718, the mobile transceiver 102 wakes up the cellular transceiver 114 from a low power mode (e.g., sleep mode), which may be performed by the main processor 104 or the baseband processor 304, depending on the embodiment. Next, the mobile transceiver 102 determines whether a cellular signal for the cellular transceiver 114 is available. This operation comprises the cellular transceiver 114 searching for a cellular signal for cellular service, and determining if any responses are received in response to the scanning.

When a cellular signal is available, processing proceeds to 720 at which the mobile transceiver 102 selects and accesses, or connects to, the cellular service, and sends a notification message (e.g., alarm or alert) to the asset tracking service 200. The notification message provides an indication that a door open event has occurred. The asset tracking log or a relevant portion of it may also be sent to the asset tracking service 200. Alternatively, the asset tracking log may be sent instead of the notification message.

At 726, after the notification message has been sent to the asset tracking service 200, a low power mode is initiated for one or more of the processor 104, cellular transceiver 114 or satellite receiver 120.

Returning to decision block 714, when a cellular signal is not available, operations proceed to 726 at which a low power mode is initiated for one or more of the processor 104, cellular transceiver 114 or satellite receiver 120.

While not shown in FIG. 7A, when the detected radiation changes from being outside of the tolerance to being within the tolerance of the constant rate, the processor 104 may update the asset tracking log stored in the memory 112 by adding a record representing a door close event. The mobile transceiver 102 may also wake up the wireless transceiver from a low power mode, and send, by the wireless transceiver, a notification message to an asset tracking service 200.

Figure 7B:
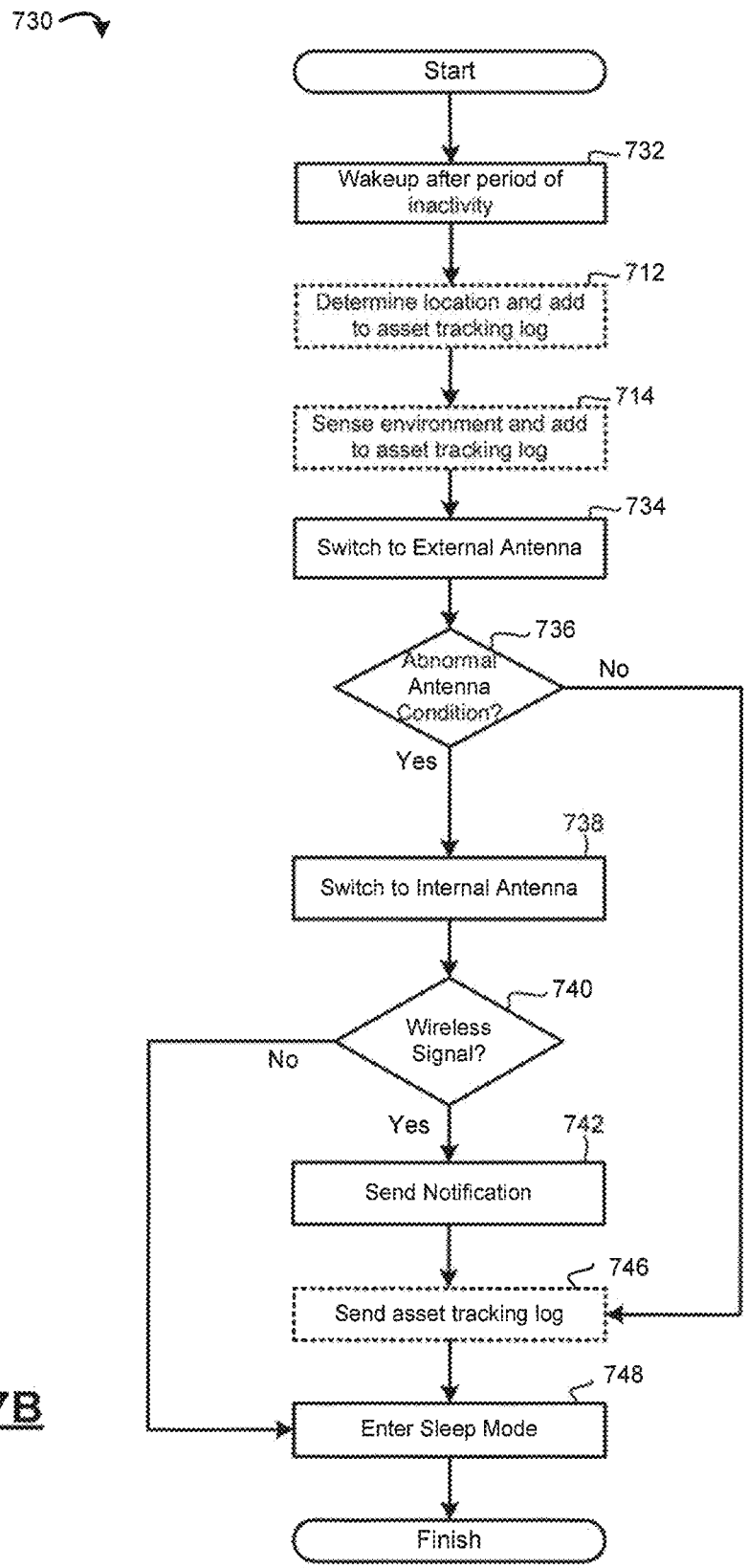

FIG. 7B shows an example flowchart of a method 730 of operating a mobile transceiver 102 such as a GNSS tracking device in accordance with another example embodiment of the present disclosure. The method may be carried out by software executed by a processor of the mobile transceiver 102. Coding of software for carrying out such a method 730 is within the scope of a person of ordinary skill in the art provided the present disclosure. The method 730 may contain additional or fewer processes than shown and/or described, and may be performed in a different order in other embodiments. Machine readable code executable by the processor to perform the method 730 may be stored in a machine readable medium such as a memory of the mobile transceiver 102.

At 732, the mobile transceiver 102 wakes up after a period of inactivity. For example, the mobile transceiver 102 may wake up from a sleep mode in which one or more of the processor 104, cellular transceiver 114 or satellite receiver 120 was in a low power mode. The wakeup may be triggered by any number of normal or abnormal events. For example, the mobile transceiver 102 may wake up in accordance with a timer or scheduled wakeup event, or a trigger/alarm caused by measurements of one or more of the sensors 130. Waking up the cellular transceiver 114 and/or satellite receiver 120 may include activating the cellular transceiver 114 and/or satellite receiver 120 from a low power mode, which may be performed by the main processor 104 or the baseband processor 304, depending on the embodiment.

At 712, the mobile transceiver 102 optionally determines its location using the satellite receiver, and stores the determined location and a time associated with the determined location in the asset tracking log.

At 714, the mobile transceiver 102 optionally senses its environment using the one or more sensors 13, and stores the measured sensor data and a time at which the sensor data was obtained in the asset tracking log.

At 734, the mobile transceiver 102 switches to an external antenna 312 of a particular wireless transceiver, such as the cellular transceiver 114, and/or switches to an external antenna of a particular wireless receiver, such as the satellite receiver 120.

At 736, the mobile transceiver 102 determines whether an indication of an abnormal antenna condition of the external antenna 312 exists. An abnormal antenna condition of the external antenna 312 includes, without limitation, damage to the external antenna 312, tampering of the external antenna 312, malfunction of the external antenna 312, and disconnection of the external antenna 312. The present embodiment, one or more of the mounting screws 610 of the transceiver housing 500 act as radioactive emitters 204 with one or more radioactive detectors 202 aligned with the mounting screws 610, for example, in the mounting holes 512 in the front panel 510 of the internal module 502. The radioactive mounting screws and pair radiation detectors 202 are used to detect that the housing 500 has been damaged or tampered with.

Determines whether an indication of an abnormal antenna condition of the external antenna 312 exists comprises the radiation detector 202 detecting radiation emitted from one or more radioactive mounting screws 610 in the housing 500. The radioactive mounting screws 610 are comprised at least partially from a radioactive alloy as described above. Next, the electrometer circuit 216 measures the detected radiation. Next, the comparator circuit 218 determines whether the measured radiation is within the tolerance of the constant rate. When the measured radiation is within the tolerance of the constant rate, this indicates the screw is present and is interpreted as a normal antenna condition. When the measured radiation is outside of the tolerance of the constant rate, this indicates the door is not present and that the housing 500 has been damaged or tampered with and is interpreted as an abnormal antenna condition. The indication is indicative but not determinative of the presence of an abnormal antenna condition of the external antenna 312.

When the mobile transceiver 102 determines that an indication of an abnormal antenna condition of the external antenna 312 exists, at 738 the mobile transceiver 102 switches to an internal antenna 310 of the particular wireless transceiver or wireless receiver.

At 740, the mobile transceiver 102 determines whether a wireless signal for the cellular transceiver 114 is available. This operation may be performed regardless of which wireless transceiver or wireless receiver has been determined to have an external antenna 312 for which an indication of an abnormal antenna condition exists in 736. This operation comprises the cellular transceiver 114 searching for a wireless signal for a wireless service, and determining if any responses are received in response to the scanning and/or measuring the signal strength of the external antenna 312 (e.g., received signal strength indicator (RSSI)).

When a wireless signal is available, processing proceeds to 742 at which the mobile transceiver 102 selects and accesses, or connects to, the wireless service, and sends a notification message (e.g., alarm or alert) to the asset tracking service 200. The notification message provides an indication that an abnormal antenna condition of the external antenna 312 for the particular wireless transceiver or wireless receiver exists.

At 746, the mobile transceiver 102 may optionally send at least a portion of the asset tracking log to the asset tracking service 200 using the wireless service. The mobile transceiver 102 may also optionally send, as part of the asset tracking log or separately, the last known position which may be the current position if the satellite receiver 120 is functional and/or able to provide the current position. Alternatively, the current position may be inferred from the cellular transceiver identifying the cellular tower or area (e.g., from a database of cellular towers) based on the mobile data connection to the cellular network 160.

At 748, after the mobile transceiver 102 has sent at least a portion of the asset tracking log to the asset tracking service 200 using the wireless service, a low power mode may be initiated for one or more of the processor 104, cellular transceiver 114 or satellite receiver 120.

Returning to decision block 740, when a wireless signal is not available, operations may proceed to 748 at which a low power mode may be initiated for one or more of the processor 104, cellular transceiver 114 or satellite receiver 12.

Figure 7C:
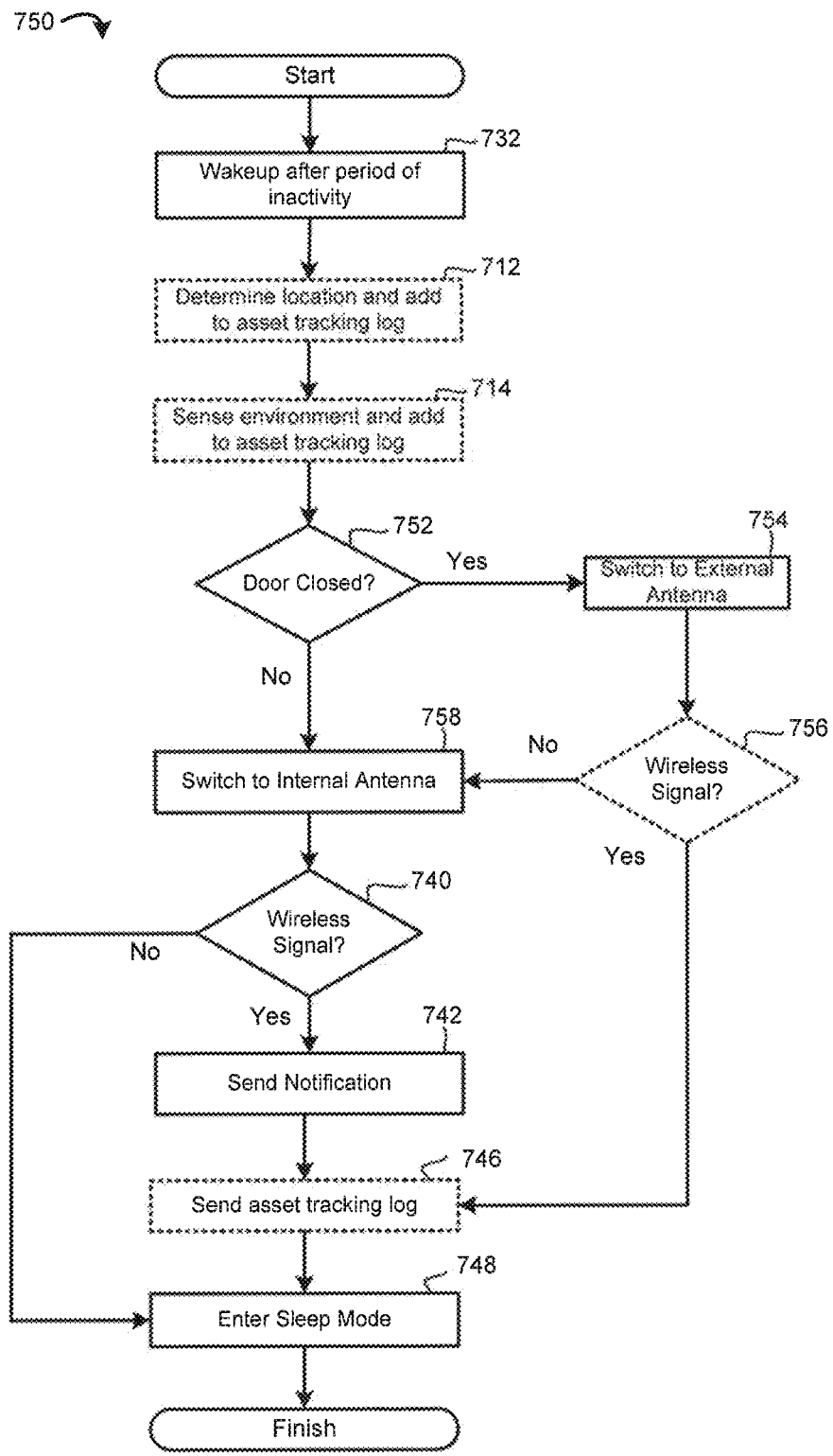

FIG. 7C shows an example flowchart of a method 750 of operating a mobile transceiver 102 such as a GNSS tracking device in accordance with a further example embodiment of the present disclosure. The method 750 is similar to the method 730 described above. The method 750 measures the signal strength of the internal antennas 310 and external antennas 312 in combination with the radiation detector 202 to determine whether the external housing module 504 and/or external antenna 312 has been damaged or tampered with, or whether damage or tampering with the external housing module 504 and/or external antenna 312 is suspected, and switch antennas if required.

At 712, the mobile transceiver 102 optionally determines its location using the satellite receiver, and stores the determined location and a time associated with the determined location in the asset tracking log.

At 714, the mobile transceiver 102 optionally senses its environment using the one or more sensors 13, and stores the measured sensor data and a time at which the sensor data was obtained in the asset tracking log.

At 752, the mobile transceiver 102 determines a state of the state of the shipping container door(s), namely whether one or more of the doors 410, 412 of the shipping container 400 are open or closed, using the radiation detector 202 as described above in connection with the operations 702, 704 and 706 of the method 700. Briefly, this comprises detecting radiation emitted from a radioactive emitter 204, measuring the detected radiation, and determining whether the measured radiation is within the tolerance of a constant rate. When the measured radiation is within the tolerance of the constant rate, this indicates the doors 410, 412 are closed. When the measured radiation is outside of the tolerance of the constant rate, this indicates one or more of the doors 410, 412 is at least partially open.

When the mobile transceiver 102 determines that one or more of the doors 410, 412 of the shipping container 400 are open, at 758 the mobile transceiver 102 switches to the internal antenna 310 and the mobile transceiver 102 proceeds with operations 740 to 748 described above.

When the mobile transceiver 102 determines that the door(s) are closed, at 754 the mobile transceiver 102 switches to the external antenna 312. At 756, the mobile transceiver 102 optionally determines whether a wireless signal for the cellular transceiver 114 is available using the external antenna 312 and/or the signal strength of the external antenna 312.

When a wireless signal is available and/or the signal strength of the external antenna 312 exceeds a threshold (decision block 756), the mobile transceiver 102 proceeds with operations 746 and 748 described above.

When a wireless signal is not available and/or the signal strength of the external antenna 312 does not exceeds the threshold (decision block 756), processing proceeds to 758 at which the mobile transceiver 102 switches to the internal antenna 310.

Figure 7D:
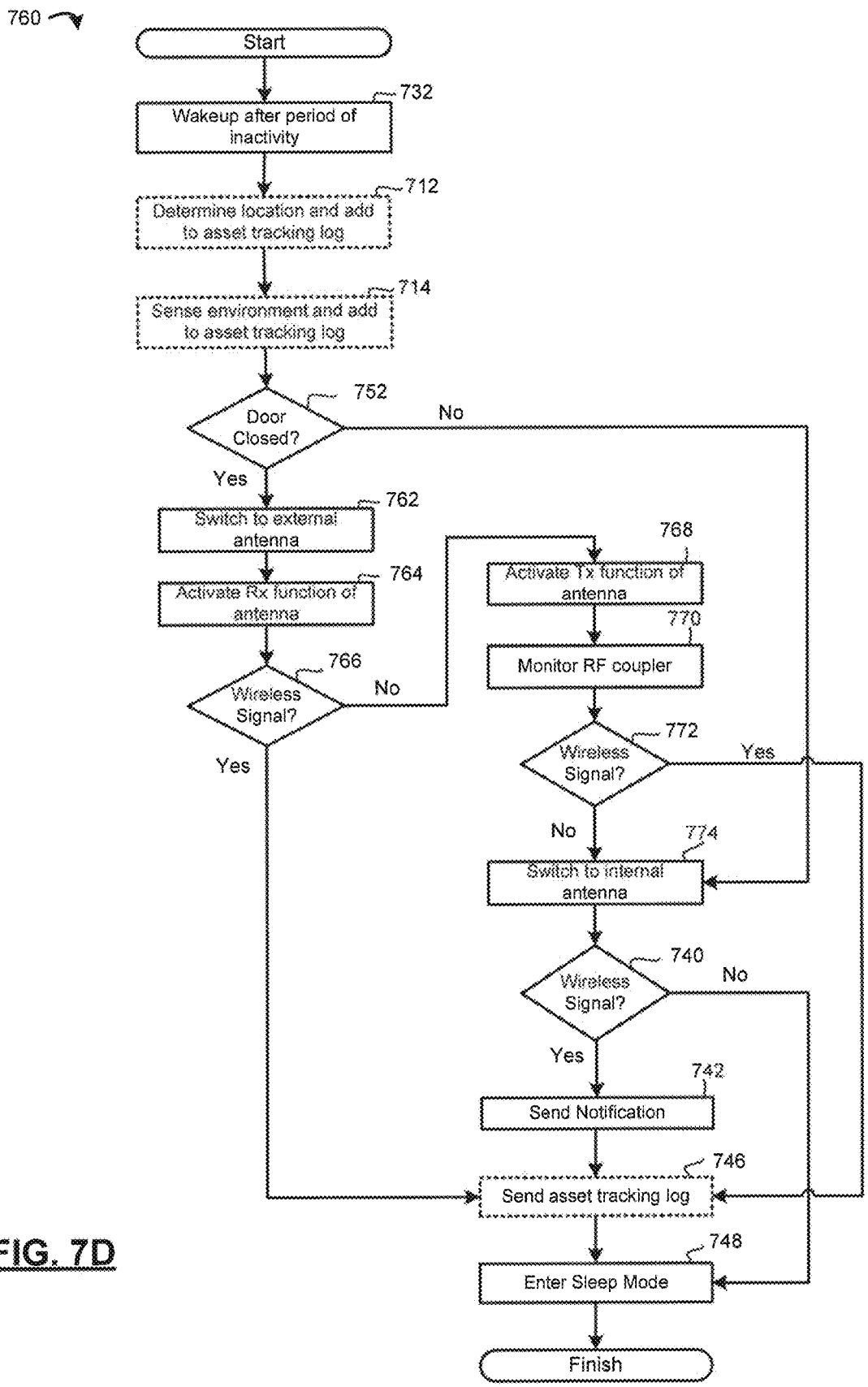

FIG. 7D shows an example flowchart of a method 760 of operating a mobile transceiver 102 such as a GNSS tracking device in accordance with yet a further example embodiment of the present disclosure. The method 750 is similar to the method 750. The method 760 uses the RF coupler 350 in combination with the radiation detector 202 to determine whether the external housing module 504 and/or external antenna 312 has been damaged or tampered with, or whether damage or tampering with the external housing module 504 and/or external antenna 312 is suspected, and switch antennas if required.

At 712, the mobile transceiver 102 optionally determines its location using the satellite receiver, and stores the determined location and a time associated with the determined location in the asset tracking log.

At 714, the mobile transceiver 102 optionally senses its environment using the one or more sensors 13, and stores the measured sensor data and a time at which the sensor data was obtained in the asset tracking log.

At 752, the mobile transceiver 102 determines a state of the state of the shipping container door(s), namely whether one or more of the doors 410, 412 of the shipping container 400 are open or closed, using the radiation detector 202 as described above When the mobile transceiver 102 determines that the door(s) are closed, at 762 the mobile transceiver 102 switches to the external antenna 312.

At 764, after the mobile transceiver 102 switches to the external antenna 312, the mobile transceiver 102 activates or performs receiving functions (Rx) using the external antenna 312 and monitors received communications using the external antenna 312 for a threshold duration.

At 766, the mobile transceiver 102 determines whether a wireless signal was detected at any time during the performance of receiving functions. When a wireless signal was detected, processing proceeds to 76646 at which the mobile transceiver 102 may optionally send the asset tracking log to the asset tracking service 200. When a wireless signal was not present, processing proceeds to 768 at which the mobile transceiver 102 activates or performs transmitting functions (Tx) using the external antenna 312.

At 770, the mobile transceiver 102 monitors the RF coupler 350 which samples transmission signals from the external antenna 312 to determine whether the external antenna 312 is actually transmitting. If the external antenna 312 is not transmitting during transmitting functions, this is an indication that the external antenna 312 is damaged, disconnected or has malfunctioned. If the external antenna 312 is transmitting during transmitting functions, this is an indication of a normal antenna condition, i.e. that the external antenna 312 is operational and functioning normally and is not damaged.

At 772, the mobile transceiver 102 determines whether a wireless signal was detected at any time during the performance of transmitting functions. When a wireless signal was detected, processing proceeds to 722 at which the mobile transceiver 102 may optionally send the asset tracking log to the asset tracking service 200. When a wireless signal was not present, processing proceeds to 774 at which the mobile transceiver 102 switches to the internal antenna 310.

While the methods 700, 730, 750 and 760 have been described independently, the methods could be executed simultaneously in parallel or sequentially in series. In addition, while the methods 700, 730, 750 and 760 have been described primarily in the context of a particular wireless transceiver, the methods can be applied to multiple wireless transceivers/receivers each having a multiple antenna configuration.

The steps and/or operations in the flowcharts and drawings described herein are for purposes of example only. There may be many variations to these steps and/or operations without departing from the teachings of the present disclosure. For instance, the steps may be performed in a differing order, or steps may be added, deleted, or modified in a manner known in the art without diminishing the outcome of the described examples herein.

While the present disclosure is described, at least in part, in terms of methods, a person of ordinary skill in the art will understand that the present disclosure is also directed to the various components for performing at least some of the aspects and features of the described methods, be it by way of hardware components, software or any combination of the two, or in any other manner. Moreover, the present disclosure is also directed to a pre-recorded storage device or other similar machine readable medium including program instructions stored thereon for performing the methods described herein.

The present disclosure may be embodied in other specific forms without departing from the subject matter of the claims. The described example embodiments are to be considered in all respects as being only illustrative and not restrictive. The present disclosure intends to cover and embrace all suitable changes in technology. The scope of the present disclosure is, therefore, described by the appended claims rather than by the foregoing description. The scope of the claims should not be limited by the embodiments set forth in the examples, but should be given the broadest interpretation consistent with the description as a whole.

The invention claimed is:

1. A method of operating a mobile transceiver, the method comprising:
    providing a mobile transceiver mounted at least partially to an interior of a shipping container, the shipping container having two doors located at one end thereof in a side-by-side arrangement, wherein a radioactive emitter is located in a mating edge of one of the two doors and a radiation detector is located in a mating edge of the other of the two doors, wherein the radioactive emitter and radiation detector are aligned with each other in response to the doors of the shipping container being closed, wherein the mobile transceiver is located on the same door as the radiation detector, the mobile transceiver comprising a processor, a memory, a wireless transceiver, a satellite receiver, the radiation detector, and a non-rechargeable battery coupled to the processor, memory, wireless transceiver, satellite receiver and radiation detector for exclusively powering the processor, memory, wireless transceiver, satellite receiver and radiation detector, the radioactive emitter being provided by a fastener formed at least partially from a radioactive alloy;
    detecting, by the radiation detector, radiation emitted from the radioactive emitter, wherein the radiation detector and the radioactive emitter are arranged such that a substantially constant rate of radiation from the radioactive emitter is detected in response to the doors of the shipping container being closed;
    in response to the detected radiation being within a tolerance of the substantially constant rate in response to the doors being closed,
        updating an asset tracking log stored in the memory by adding a record representing a door close event;
    in response to the detected radiation being outside of the tolerance of the substantially constant rate in response to at least one of the door being at least partially open,
        waking up the processor and satellite receiver from a low power mode,
        determining, via the satellite receiver, a location of the mobile transceiver, and
        at least one of updating the asset tracking log stored in the memory by adding a record, which record stores the determined location and a time associated with the determined location, representing a door open event, or sending, by the wireless transceiver, a notification message to an asset tracking service.

2. The method of claim 1, further comprising:
    in response to the detected radiation changing from being outside of the tolerance to being within the tolerance of the substantially constant rate,
        updating the asset tracking log stored in the memory by adding a record representing a door close event.

3. The method of claim 2, further comprising:
    in response to the detected radiation changing from being outside of the tolerance to being within the tolerance of the substantially constant rate,
        waking up the wireless transceiver from a low power mode, and
        sending, by the wireless transceiver, a notification message to an asset tracking service.

4. The method of claim 1, sending, by the wireless transceiver, a notification message to an asset tracking service, wherein the notification message comprises the asset tracking log.

5. The method of claim 1, further comprising: sending, by the wireless transceiver, a notification message to an asset tracking service,
    before sending the notification message to the asset tracking service,
        measuring, by one or more sensors, an environment of the mobile transceiver, and updating the asset tracking log to include sensor data representing the environment of the mobile transceiver.

6. The method of claim 1, further comprising: sending, by the wireless transceiver, a notification message to an asset tracking service,
initiating a low power mode for the processor and satellite receiver after sending the notification message to the asset tracking service.

7. The method of claim 1, wherein the radiation detector comprises an ionization chamber.

8. The method of claim 1, further comprising:
initiating a low power mode for the processor and satellite receiver in response to updating the asset tracking log stored in the memory by adding a record representing a door close event.

9. The method of claim 1, wherein the mobile transceiver comprises a two-part housing configured to be mounted through the other of the two doors of the shipping container, wherein the housing carries the processor, memory, wireless transceiver, satellite receiver and radiation detector, wherein the housing comprises an internal module configured to be mounted on an inside surface of the other of the two doors of the shipping container and an external module configured to be mounted on an outside surface of the other of the two doors of the shipping container, wherein the external module carries one or more external antennas for use in response to the doors of the shipping container being closed, wherein the internal module carries one or more internal antennas for use in response to the doors of the shipping container being at least partially open.

10. A mobile transceiver, comprising:
a processor;
a memory coupled to the processor;
a wireless transceiver coupled to the processor;
a satellite receiver coupled to the processor;
a radiation detector coupled to the processor;
a non-rechargeable battery coupled to the processor, memory, wireless transceiver, satellite receiver and radiation detector for exclusively powering the processor, memory, wireless transceiver, satellite receiver and radiation detector;
wherein the memory includes executable instructions that, when executed by the processor, cause the mobile transceiver to:
detect, by the radiation detector, radiation emitted from a radioactive emitter,
the mobile transceiver being mounted at least partially to an interior of a shipping container, the shipping container having two doors located at one end thereof in a side-by-side arrangement, wherein the radioactive emitter is located in a mating edge of one of the two doors and the radiation detector is located in a mating edge of the other of the two doors, wherein the radioactive emitter and radiation detector are aligned with each other in response to the doors of the shipping container being closed, wherein the mobile transceiver is located on the same door as the radiation detector, the radioactive emitter being provided by a fastener formed at least partially from a radioactive alloy,
wherein the radiation detector and the radioactive emitter are arranged such that a substantially constant rate of radiation from the radioactive emitter is detected in response to the doors of shipping container being closed;
in response to the detected radiation being within a tolerance of the substantially constant rate in response to the doors being closed,
updating an asset tracking log stored in the memory by adding a record representing a door close event;
in response to the detected radiation being outside of the tolerance of the substantially constant rate in response to at least one of the doors being at least partially open,
wake up the processor and satellite receiver from a low power mode,
determine, via the satellite receiver, a location of the mobile transceiver, and
at least one of update the asset tracking log stored in the memory by adding a record, which record stores the determined location and a time associated with the determined location, representing a door open event, or send, by the wireless transceiver, a notification message to an asset tracking service.

11. The mobile transceiver of claim 10, wherein the processor receives a first interrupt signal from the radiation detector in response to the detected radiation being outside a tolerance of the substantially constant rate, and wherein the processor receives a second interrupt signal from the radiation detector in response to the detected radiation changing from being outside of the tolerance and being within the tolerance of the substantially constant rate.

12. The mobile transceiver of claim 11, wherein the first interrupt signal indicates a misalignment between the radioactive emitter and radiation detector, and the second interrupt signal indicates an alignment between the radioactive emitter and radiation detector.

13. The mobile transceiver of claim 11, wherein the first interrupt signal indicates a door open condition and the second interrupt signal indicates a door closed condition.

14. The mobile transceiver of claim 10, wherein the radioactive alloy is an alloy of steel and Americium-241 or an alloy of steel and Americium-241 with trace amounts of one or more of Iodine-131 or Strontium-90.

15. The mobile transceiver of claim 10, wherein the radiation detector comprises an ionization chamber.

16. The mobile transceiver of claim 10, wherein the executable instructions cause the mobile transceiver to:
initiate a low power mode for the processor and satellite receiver in response to updating the asset tracking log stored in the memory by adding a record representing a door close event.

17. A non-transitory machine readable medium having tangibly stored thereon executable instructions for performing a method of operating a mobile transceiver, the mobile transceiver comprising at least a processor, a memory, a wireless transceiver, a satellite receiver a radiation detector, and a non-rechargeable battery coupled to the processor, memory, wireless transceiver, satellite receiver and radiation detector for exclusively powering the processor, memory, wireless transceiver, satellite receiver and radiation detector, wherein the executable instructions, when executed by the processor, cause the mobile transceiver to:
detect, by the radiation detector, radiation emitted from a radioactive emitter,
the mobile transceiver being mounted at least partially to an interior of a shipping container, the shipping container having two doors located at one end thereof in a side-by-side arrangement, wherein the radioactive emitter is located in a mating edge of one of the two doors and the radiation detector is located in a mating edge of the other of the two doors, wherein the radioactive emitter and radiation detector are aligned with each other in response to the doors of the shipping container being closed, wherein the mobile transceiver is located on the same door as the radiation detector, the radioactive emitter being provided by a fastener formed at least partially from a radioactive alloy, wherein the radiation detector and the radioactive emitter are arranged such that a substantially constant rate of radiation from the radioactive emitter is detected in response to the doors of the shipping container being closed;

in response to the detected radiation being within a tolerance of the substantially constant rate in response to the doors being closed,
update an asset tracking log stored in the memory by adding a record representing a door close event;

in response to the detected radiation being outside of the tolerance of the substantially constant rate in response to at least one of the doors being at least partially open,
wake up the processor and satellite receiver from a low power mode,
determine, via the satellite receiver, a location of the mobile transceiver, and
at least one of update the asset tracking log stored in the memory by adding a record, which record stores the determined location and a time associated with the determined location, representing a door open event, or send, by the wireless transceiver, a notification message to an asset tracking service.

18. The non-transitory machine readable medium of claim 17, wherein the radiation detector comprises an ionization chamber.

19. The non-transitory machine readable medium of claim 17, wherein the executable instructions cause the mobile transceiver to:
initiate a low power mode for the processor and satellite receiver in response to updating the asset tracking log stored in the memory by adding a record representing a door close event.

20. A method of operating a mobile transceiver, the method comprising:
providing a mobile transceiver mounted at least partially to an interior of a door of a shipping container, wherein one of a radioactive emitter and a radiation detector is located in a door frame of the shipping container and the other of the radioactive emitter and the radiation detector is located in an outer edge of the door, wherein the radioactive emitter and radiation detector are aligned with each other in response to the door of the shipping container being closed, the mobile transceiver comprising a processor, a memory, a wireless transceiver, a satellite receiver, the radiation detector, and a non-rechargeable battery coupled to the processor, memory, wireless transceiver, satellite receiver and radiation detector for exclusively powering the processor, memory, wireless transceiver, satellite receiver and radiation detector, the radioactive emitter being provided by a fastener formed at least partially from a radioactive alloy;

detecting, by the radiation detector, radiation emitted from the radioactive emitter, wherein the radiation detector and the radioactive emitter are arranged such that a substantially constant rate of radiation from the radioactive emitter is detected in response to the door of the shipping container being closed;

in response to the detected radiation being within a tolerance of the substantially constant rate in response to the door being closed,
updating an asset tracking log stored in the memory by adding a record representing a door close event;

in response to the detected radiation being outside of the tolerance of the substantially constant rate in response to the door being at least partially open,
waking up the processor and satellite receiver from a low power mode,
determining, via the satellite receiver, a location of the mobile transceiver, and
at least one of updating the asset tracking log stored in the memory by adding a record, which record stores the determined location and a time associated with the determined location, representing a door open event, or sending, by the wireless transceiver, a notification message to an asset tracking service.

21. The method of claim 20, further comprising:
initiating a low power mode for the processor and satellite receiver in response to updating the asset tracking log stored in the memory by adding a record representing a door close event.

22. A mobile transceiver, comprising:
a processor;
a memory coupled to the processor;
a wireless transceiver coupled to the processor;
a satellite receiver coupled to the processor;
a radiation detector coupled to the processor;
a non-rechargeable battery coupled to the processor, memory, wireless transceiver, satellite receiver and radiation detector for exclusively powering the processor, memory, wireless transceiver, satellite receiver and radiation detector;
wherein the memory includes executable instructions that, when executed by the processor, cause the mobile transceiver to:
detect, by the radiation detector, radiation emitted from a radioactive emitter,
the mobile transceiver being mounted at least partially to an interior of a door of a shipping container, wherein one of the radioactive emitter and the radiation detector is located in a door frame of the shipping container and the other of the radioactive emitter and the radiation detector is located in an outer edge of the door, wherein the radioactive emitter and radiation detector are aligned with each other in response to the door of the shipping container being closed, the radioactive emitter being provided by a fastener formed at least partially from a radioactive alloy,
wherein the radiation detector and the radioactive emitter are arranged such that a substantially constant rate of radiation from the radioactive emitter is detected in response to the door of the shipping container being closed;

in response to the detected radiation being within a tolerance of the substantially constant rate in response to the door being closed,
update an asset tracking log stored in the memory by adding a record representing a door close event;

in response to the detected radiation being outside of the tolerance of the substantially constant rate in response to the door being at least partially open;
wake up the processor and satellite receiver from a low power mode, determine, via the satellite receiver, a location of the mobile transceiver, and at least one of update the asset tracking log stored in the memory by adding a record, which record stores the determined location and a time associated with the determined location, representing a door open event, or send, by the wireless transceiver, a notification message to an asset tracking service.

23. The mobile transceiver of claim 22, wherein the executable instructions cause the mobile transceiver to:

initiate a low power mode for the processor and satellite receiver in response to updating the asset tracking log stored in the memory by adding a record representing a door close event.

24. A non-transitory machine readable medium having tangibly stored thereon executable instructions for performing a method of operating a mobile transceiver, the mobile transceiver comprising at least a processor, a memory, a wireless transceiver, a satellite receiver a radiation detector, and a non-rechargeable battery coupled to the processor, memory, wireless transceiver, satellite receiver and radiation detector for exclusively powering the processor, memory, wireless transceiver, satellite receiver and radiation detector, wherein the executable instructions, when executed by the processor, cause the mobile transceiver to:

detect, by the radiation detector, radiation emitted from a radioactive emitter, the mobile transceiver being mounted at least partially to an interior of a door of a shipping container, wherein one of the radioactive emitter and the radiation detector is located in a door frame of the shipping container and the other of the radioactive emitter and the radiation detector is located in an outer edge of the door, wherein the radioactive emitter and radiation detector are aligned with each other in response to the door of the shipping container being closed, the radioactive emitter being provided by a fastener formed at least partially from a radioactive alloy, wherein the radiation detector and the radioactive emitter are arranged such that a substantially constant rate of radiation from the radioactive emitter is detected in response to the door of the shipping container being closed;

in response to the detected radiation being within a tolerance of the substantially constant rate in response to the door being closed, update an asset tracking log stored in the memory by adding a record representing a door close event;

in response to the detected radiation being outside of the tolerance of the substantially constant rate in response to the door being at least partially open, waking up the processor and satellite receiver from a low power mode, determining, via the satellite receiver, a location of the mobile transceiver, and at least one of update the asset tracking log stored in the memory by adding a record, which record stores the determined location and a time associated with the determined location, representing a door open event, or send, by the wireless transceiver, a notification message to an asset tracking service.

25. The non-transitory machine readable medium of claim 24, wherein the executable instructions cause the mobile transceiver to:

initiate a low power mode for the processor and satellite receiver in response to updating the asset tracking log stored in the memory by adding a record representing a door close event.

* * * * *